US012268752B2

(12) United States Patent
Zhu et al.

(10) Patent No.: US 12,268,752 B2
(45) Date of Patent: Apr. 8, 2025

(54) NON-NATURAL AMATOXIN-TYPE ANTIBODY CONJUGATE

(71) Applicant: SICHUAN BAILI PHARMACEUTICAL CO. LTD., Sichuan (CN)

(72) Inventors: Yi Zhu, Sichuan (CN); Jie Li, Sichuan (CN); Yongguo Yu, Sichuan (CN); Weijia Liu, Sichuan (CN); Shi Zhuo, Sichuan (CN)

(73) Assignee: SYSTIMMUNE, INC., Redmond, WA (US)

( * ) Notice: Subject to any disclaimer, the term of this patent is extended or adjusted under 35 U.S.C. 154(b) by 1256 days.

(21) Appl. No.: 16/975,406

(22) PCT Filed: Aug. 18, 2018

(86) PCT No.: PCT/CN2018/101213

§ 371 (c)(1),
(2) Date: Aug. 25, 2020

(87) PCT Pub. No.: WO2019/034175

PCT Pub. Date: Feb. 21, 2019

(65) Prior Publication Data

US 2021/0030887 A1 Feb. 4, 2021

(30) Foreign Application Priority Data

Aug. 18, 2017 (CN) ......................... 201710710293.6

(51) Int. Cl.
*A61K 47/68* (2017.01)
*C07K 16/32* (2006.01)

(52) U.S. Cl.
CPC ...... *A61K 47/6831* (2017.08); *A61K 47/6849* (2017.08); *C07K 16/32* (2013.01)

(58) Field of Classification Search
CPC ........................ A61K 47/6831; A61K 47/6803
See application file for complete search history.

(56) References Cited

U.S. PATENT DOCUMENTS

2012/0100161 A1 4/2012 Faulstich

FOREIGN PATENT DOCUMENTS

| | | | | |
|---|---|---|---|---|
| CN | 104470891 | Y | 2/2004 | |
| CN | 102387815 | A | 3/2012 | |
| CN | 103442736 | Y | 9/2016 | |
| CN | 103153345 | Y | 10/2016 | |
| WO | WO-2012041504 | A1 * | 4/2012 | ....... A61K 47/48415 |
| WO | WO-2012119787 | A1 * | 9/2012 | ............. A61K 38/12 |
| WO | WO2017089607 | A | 6/2017 | |
| WO | WO-2017149077 | A1 * | 9/2017 | ............. A61K 38/12 |
| WO | WO-2018086139 | A1 * | 5/2018 | ........... A61K 31/337 |
| WO | WO-2019030173 | A1 * | 2/2019 | ......... A61K 47/6831 |
| WO | WO-2019047941 | A1 * | 3/2019 | ............. A61K 38/12 |

OTHER PUBLICATIONS

Weiland et al.(Biochemistry, 1983, vol. 22, pp. 1264-1271). (Year: 1983).*

* cited by examiner

*Primary Examiner* — Karen A. Canella
(74) *Attorney, Agent, or Firm* — EpiMED LLC

(57) ABSTRACT

Disclosed is a non-natural amatoxin-type antibody conjugate, said conjugate similar to the natural amatoxin is linked to a biopharmaceutically acceptable salt with a target biomolecule so as to obtain stability in blood plasma, and efficiently kill tumor cells in cells.

17 Claims, No Drawings

NON-NATURAL AMATOXIN-TYPE ANTIBODY CONJUGATE

TECHNICAL FIELD

The present invention relates to a bicyclic octapeptide derivative, which can be conjugated to a corresponding target-binding group in a special chemical structure. This structure is stable in blood plasma and decomposed into an active pharmaceutical ingredient in a specific biological environment, thereby maximizing killing effects on target cells and minimizing toxic side effects on non-target cells, which can be used in the treatment of various malignant tumors.

BACKGROUND ART

Amanitin is one of the amanita peptide toxins isolated from lethal mushrooms, and is a bicyclic peptide composed of eight amino acids. There are nine natural amanitins which have been isolated and purified, which are respectively α-amanitin, β-amanitin, γ-amanitin, ε-amanitin, amanin, amaninamide, amanullin, amanullinic acid and proamanullin, wherein α-amanitin and β-amanitin are the main toxins causing death. Amanitin is a class of slow-acting toxins, and can inhibit the transcription of eukaryotic RNA polymerase II and RNA polymerase III, leading to protein deficiency and cell death. This class of toxins have an extremely high inhibitory effect on RNA polymerase II, and the $K_D$ thereof can reach 3 nM. The toxins are repeatedly absorbed in the body due to the enterohepatic circulation in the gastrointestinal tract, and can cause sustained serious damage to organs, such as liver, kidney, heart and lung.

After amanitin is conjugated to a large biomolecular carrier (such as an antibody molecule), the toxicity of the amanitin is greatly reduced and even the amanitin is relatively non-toxic; and the cytotoxicity of amanitin can be observed only after the biomolecular carrier is removed in a specific physiological environment.

According to the research from the Theodor Wieland team, when the sulphoxide structure in the natural amanitin is changed to a sulphur element, the toxicity to cells of the non-natural amanitin formed thereby changes little. A natural-amanitin molecule is conjugated to a monoclonal antibody by Heidelberg Pharmaceutical Co., Ltd., Germany, thereby obtaining a drug molecule having an anti-tumor activity.

In the present invention, a non-natural amanitin similar to a natural amanitin in toxicity is conjugated to a biomolecule capable of binding to a target through a biopharmaceutically acceptable connecting structure, so as to obtain a compound which is stable in plasma and can efficiently kill tumor cells in cells.

Definitions

According to standards and practices in the art, the symbol

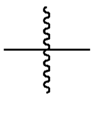

used in formulas and tables represents a bond used as a point for connecting a moiety or a substituent to the core of a compound structure.

According to standards and practices in the art, hetero (atom, alkyl, aryl, cyclo) refers to a corresponding chemical structure containing an atom (or atoms) other than carbon.

SUMMARY OF THE INVENTION

The present invention provides a conjugate of a bicyclic octapeptide amanitin derivative and a biomacromolecule, which is stable in the blood circulation system, and is cleaved after endocytosis by target cells, thereby releasing the amanitin derivative as a RNA polymerase inhibitor, and produces a strong toxicity to the cells through specific inhibition of mRNA synthesis in eukaryotes, and the conjugate is specifically a toxin conjugate of structural formula (I):

(I)

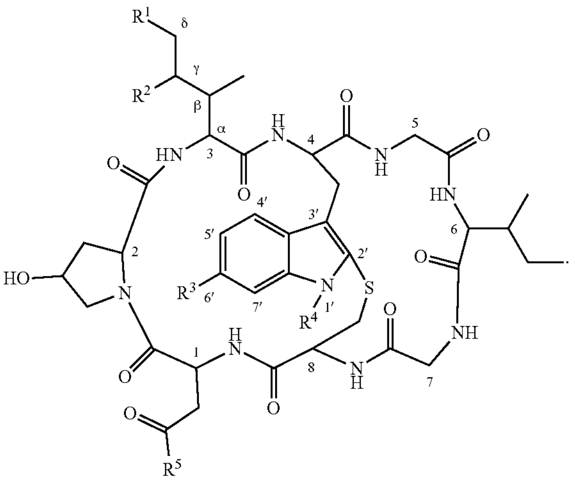

wherein:

$R^1$ is H, —OH or —O-L-A;

$R^2$ is H and —OH;

$R^3$ is $OC_{1-6}$ alkyl;

$R^4$ is H or -L-A;

$R^5$ is —$NH_2$, —OH, —NH-L-A or —O-L-A;

wherein O is an oxygen atom, N is a nitrogen atom and H is a hydrogen atom.

A is a biomacromolecule moiety binding to a target site; as a preferred embodiment, the L comprises the following structure:

$$-L_1-[L_2]_m-[AA]_n-L_3-$$

wherein: $L_1$ is a linker for connecting to biomacromolecule A; $L_2$ is a spacer, and $L_2$ is a fragment connecting $L_1$ to AA; m is an integer from 1-6; $L_3$ connects to the toxin shown in structural formula (I); AA is a fragment consisting of 1 to 6 amino acids, and n is 0 or 1.

As a preferred embodiment, the A is a biomacromolecule moiety binding to a target site, and includes an antibody or antigen-binding fragments thereof, an antibody-like protein, a nucleic acid aptamer, etc.

As a preferred embodiment, the biomacromolecule binding to the target site is an antibody or an antigen-binding fragment thereof, which is selected from a chimeric antibody, a deimmunized antibody, a humanized antibody, a human antibody, a diabody, a triabody and a nanobody.

Further preferably, the antigen-binding fragment is selected from the group consisting of Fab, F(ab'), Fd, Fv, a single-chain Fv and a disulfide-linked Fv(dsFv).

As a preferred embodiment, one and only one of the $R^1$, $R^4$ and $R^5$ contains a -L-A structure.

As a preferred embodiment, the $L_1$ is a linker for connecting to biomacromolecule A, and is selected from:

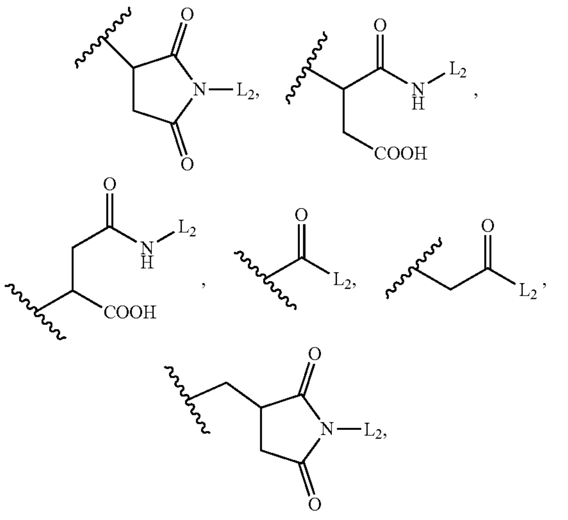

etc.; wherein a wavy line connects to biomacromolecule A.

As a preferred embodiment, the $L_2$ is a spacer selected from one or more of identical or different combinations of a substituted or unsubstituted C1-C6 alkyl, a substituted or unsubstituted C3-C20 cycloalkyl, a substituted or unsubstituted C3-C20 heterocycloalkyl, a substituted or unsubstituted C5-C20 aryl, a substituted or unsubstituted C5-C20 heteroaryl and $-(CH_2CH_2O)a-$ (wherein a is an integer from 1 to 20), and the spacers are connected with one another through a reasonable chemical bond.

Further preferably, the substituent is selected from one or more of identical or different combinations of a hydroxyl group, a sulfydryl group, halogen, a carboxyl group, an amino group, a phosphate group, a nitro group, a cyano group, a sulfo group, a substituted or unsubstituted C1-C6 alkyl, etc.

Further preferably, the substituent is selected from one or more of identical or different combinations of a hydroxyl group, a sulfydryl group, halogen, a carboxyl group, an amino group, a phosphate group, a nitro group, a cyano group, a sulfo group, etc.

As a preferred embodiment, AA is a fragment consisting of 1 to 6 amino acids, which are L-amino acids selected from glycine, alanine, valine, leucine, isoleucine, phenylalanine, proline, tryptophan, serine, tyrosine, cysteine, methionine, asparagine, glutamine, threonine, aspartate, glutamate, lysine, arginine, histidine etc., and further preferably, phenylalanine, citrulline, valine, lysine, serine, glutamate, aspartate and glycine.

As a preferred embodiment, the $L_3$ is selected from

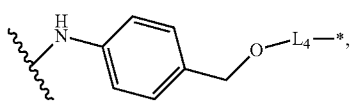

-continued

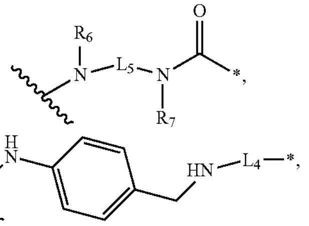

any linking group that connects to the toxin, etc.

wherein a wavy line connects to AA and an asterisk connects to the toxin shown in structural formula (I).

Further preferably, the L4 is selected from a carbonyl group or a single bond.

Further preferably, the R6 and R7 are each independently selected from hydrogen, C1-C6 alkyl, etc.

Further preferably, the L5 is C2-C12 alkyl.

As a preferred embodiment, the drug contains the toxin conjugate of structural formula (I) described in any one of the above, or a salt thereof.

As a preferred embodiment, use of the toxin conjugate of structural formula (I) described in any one of the above, or a salt thereof in the preparation of an anti-tumor drug or an anti-cancer drug is disclosed.

As a preferred embodiment, the anti-tumor drug or anti-cancer drug is an anti-lung cancer drug, an anti-renal cancer drug, an anti-urethral cancer drug, an anti-colorectal cancer drug, an anti-prostate cancer drug, an anti-glioblastoma drug, an anti-ovarian cancer drug, an anti-pancreatic cancer drug, an anti-breast cancer drug, an anti-melanoma drug, an anti-liver cancer drug, an anti-bladder cancer drug, an anti-malignant lymphoma drug, an anti-leukemia drug, an anti-gastric cancer drugs or an anti-esophageal cancer drug.

Universal abbreviations and symbols:

g: gram
mg: milligram
min: minute
mL: milliliter
mol: molar
° C.: degrees centigrade
Boc: tert-butoxycarbonyl
PyBOP: 1H-benzotriazole-1-yl-oxytripyrrolidinophosphonium hexafluorophosphate
Cit: citrulline
$CO_2$: carbon dioxide
DCM: dichloromethane
DIPEA: diisopropylethylamine
DMF: dimethylformamide
DMSO: dimethyl sulphoxide
DPBS: Dulbecco's phosphate buffer solution
DTPA: diethylene triamine penlaacetic acid
DTT: dithiothreitol
EA: ethyl acetate
EDTA: ethylenediamine tetraacetic acid
FBS: fetal bovine serum
HATU: O-(7-azobenzotriazole)-N,N,N,N-tetramethyluronium hexafluophosphate
$H_2O$: water
HOBt: 1-hydroxybenzotriazole
mAb: monoclonal antibody
MEM: minimum essential medium
MTS: 3-(4,5-dimethyl thiazole-2-yl)-5-(3-carboxymethoxyphenyl)-2-(4-sulfophenyl)-2H-tetrazolium, inner salt
MTT: 3-(4,5-dimethyl thiazole-2)-2,5-diphenyltetrazolium bromide PAB: para-amino benzyloxy
PBS: phosphate buffer solution
Sodium Pyruvate: Na pyruvate
THF: tetrahydrofuran
TLC: thin-layer chromatography
Tris: trishydroxymethyl aminomethane
Val: valine
Trt-Cl: triphenylmethyl chloride
TBTU: O-(1H-benzotriazole-1-yl)-N,N,N',N'-tetramethyluronium tetrafluoroborate
HOBT: 1-hydroxybenzotriazole
TFA: trifluoroacetic acid
TBS-Cl: tert-butyldimethylsilyl chloride
HOSu: N-hydroxysuccinimide
$Na_2CO_3$: sodium carbonate
EDCI: 1-(3-dimethylaminopropyl)-3-ethylcarbodiimide hydrochloride
CuBr: copper bromide

DETAILED DESCRIPTION OF EMBODIMENTS

The present invention is further illustrated by combining particular examples below. These examples are only used to describe the present invention but not to limit the scope of the present invention. Unless otherwise defined, all professional and scientific terms used herein have the same meanings as those commonly understood by a person skilled in the art. In addition, any methods and materials similar or equivalent to the contents described herein can all be applied in the method of the present invention. The preferred embodiments and materials described herein are meant for exemplary purposes only.

Example 1 Synthesis of Small Molecule Payload Ama-0301

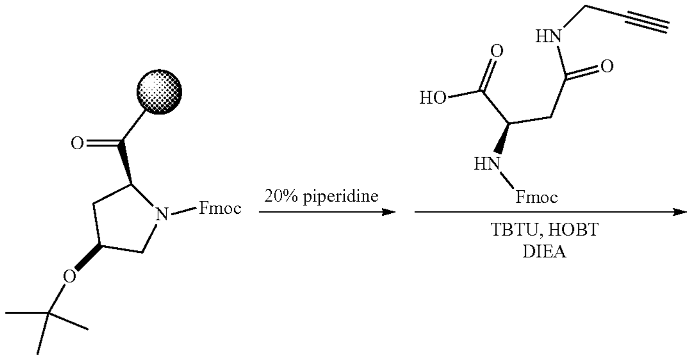

01

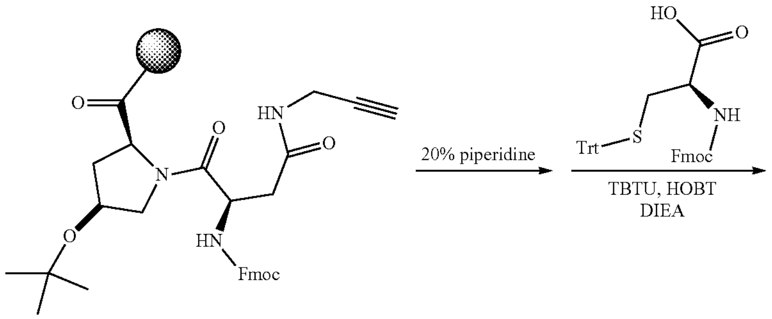

02

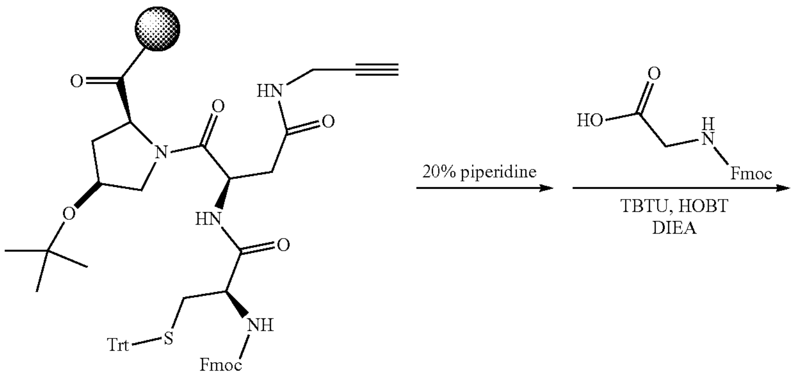

03

-continued
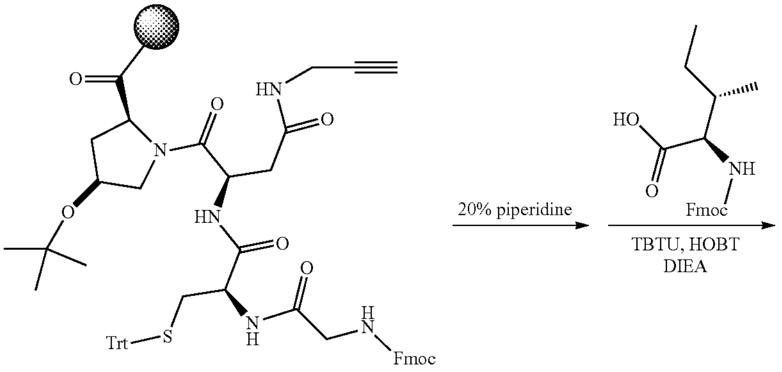
04
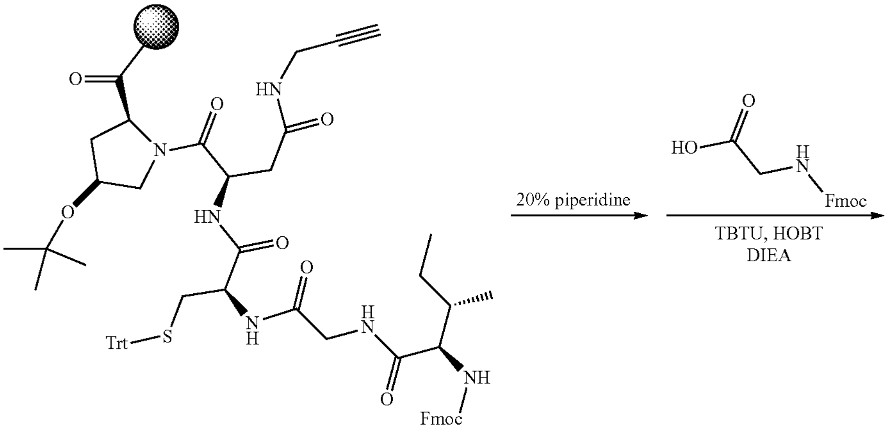
05
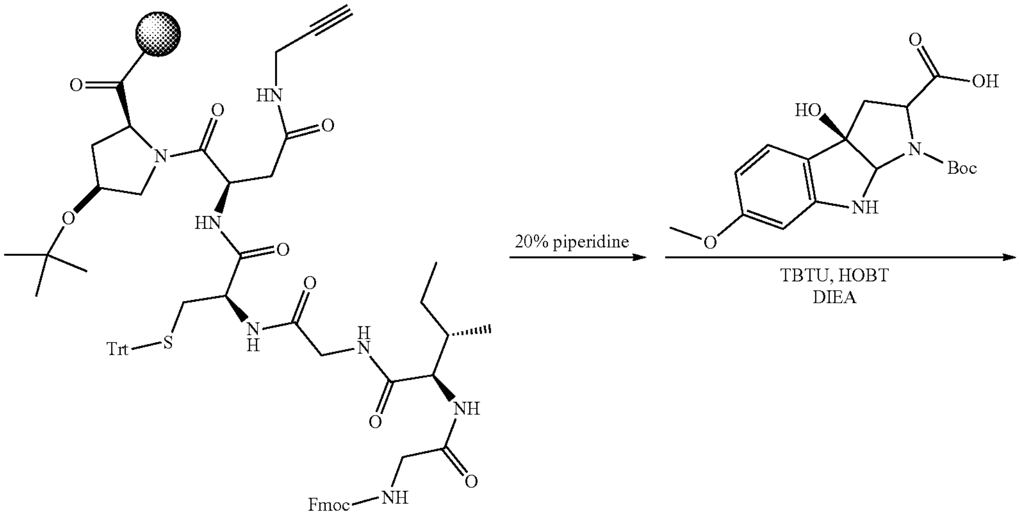
06

-continued

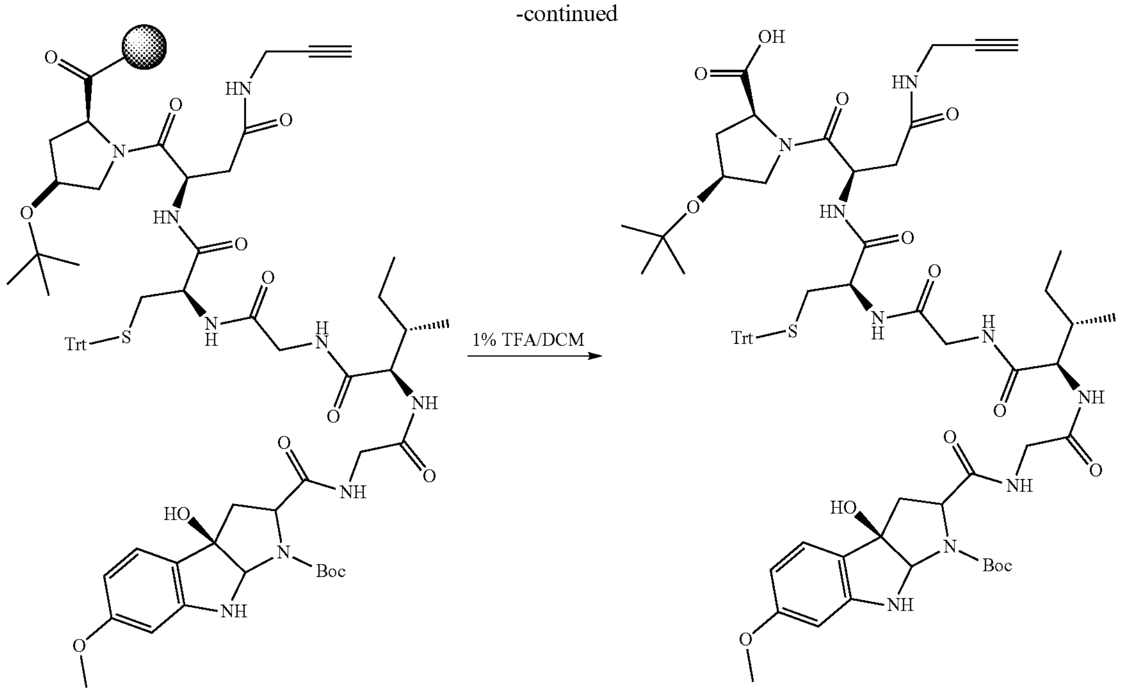

07 08

1) Solid Phase Synthesis of Intermediate 08

N-fluorenylmethoxycarbonyl-O-tert-butyl-L-hydroxy-proline preloaded resin, which was used as a raw material, was treated with 20% piperidine (adding 20 ml of 20% piperidine to 1 g of the resin) to remove protecting group Fmoc, and washed with DMF for 5 times until a neutral pH was achieved. Then the DMF, which was used as a solution (20 ml/g), sequentially added with Fmoc-N-propinyl-L-asparagine (Fmoc-Asn(Trt)-OH) (3 eq), TBTU (2.5 eq), HOBT (1.8 eq) and DIPEA (6 eq), reacted for 2 h at room temperature (28° C.), and then washed for 3 times with DMF (for each time, adding 20 ml of DMF to 1 g of the resin), followed by connecting to amino acids according to the previous operation. After the final connection was completed, the resultant was cleaved from the resin by using 1% TFA in dichloromethane solution (for each time, adding 20 ml to 1 g of the resin; 1% TFA for 5 min; repeated three times); the solution was removed by rotary evaporation; and stirring was performed with methyl tert-butyl ether for crystallization so as to obtain compound 08, with a total yield of about 43% and a high purity of 81.3%. MS: $[M+H]^+$ 1244.6521

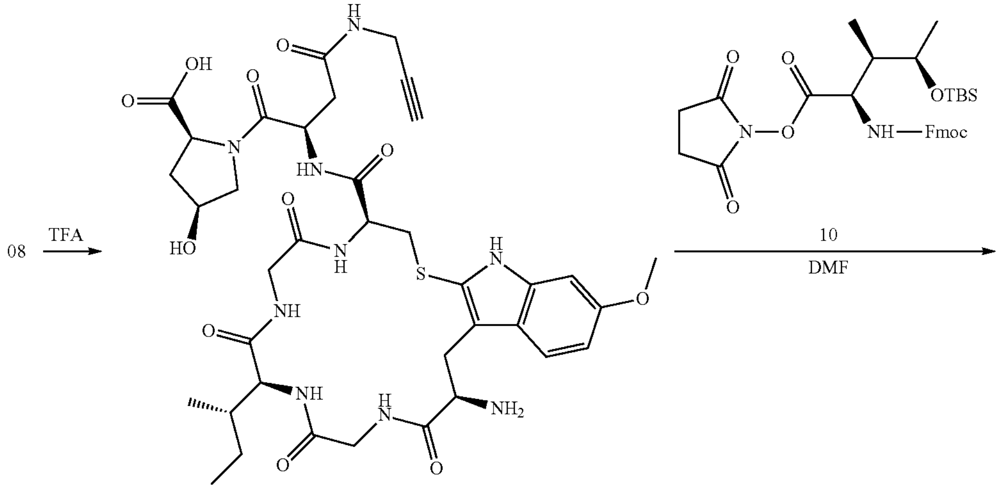

09

-continued
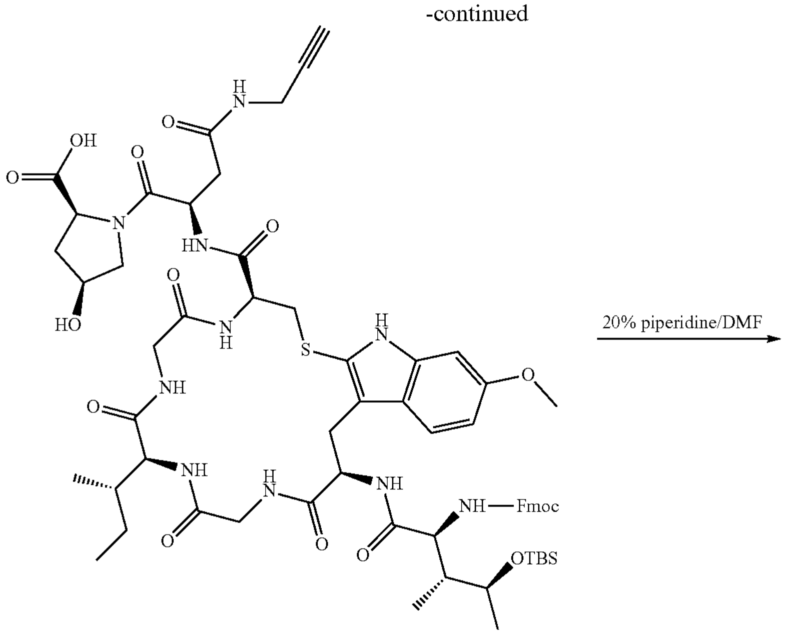
11
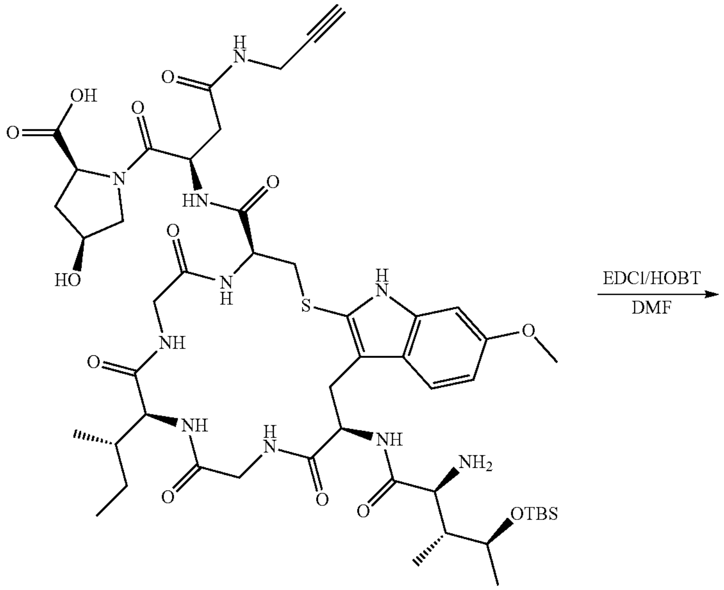
12

-continued

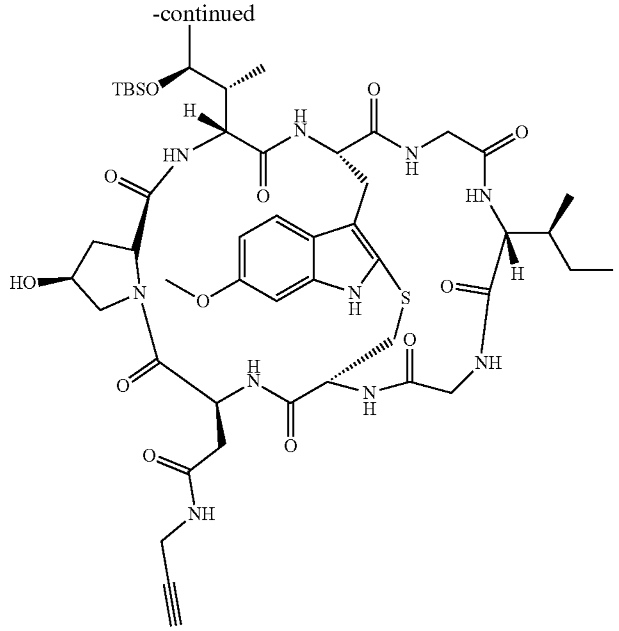

13

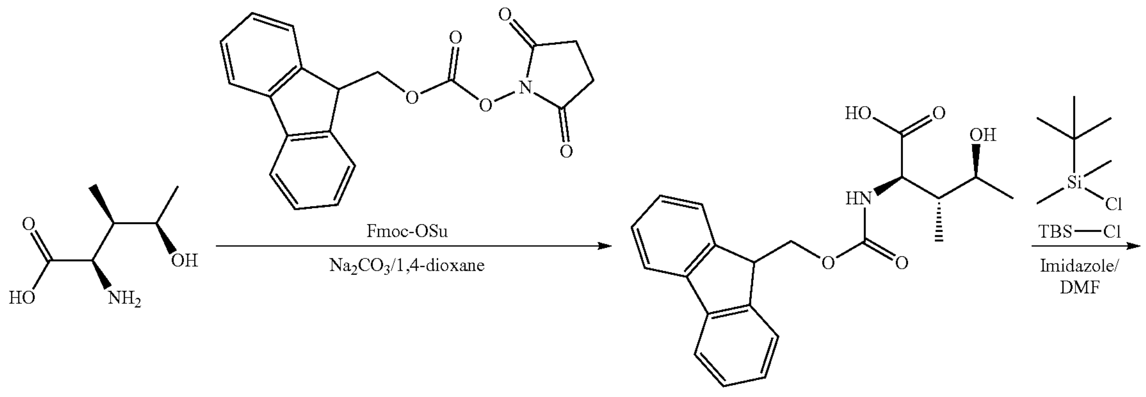

14

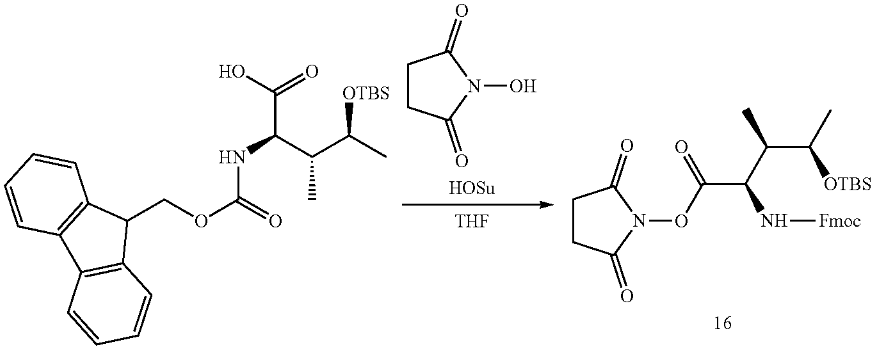

15

16

2) Synthesis of Compound 09

8 g of compound 08 crude product was dissolved with TFA (10 ml/g), and then stirred and reacted 5 h at room temperature; TFA was removed under reduced pressure at 50° C.; and purification was performed using preparative liquid chromatography to obtain about 3.8 g of pure product of compound 09, with a yield of 71% and a purity of 96.4%. MS: $[M+H]^+$ 828.3241

3) Synthesis of Compound 14

2.94 g of (4S)-hydroxylisoleucine, 40 ml of 1,4-dioxane and ml of saturated sodium carbonate solution were added to a 250 ml single necked flask, and homogeneously stirred, followed by portion-wise addition of Fmoc-OSu. After 10 min, stirring was continued at room temperature for 12 h until the reaction of raw materials was completed. 50 ml of water was added to the reaction liquid and 5% citric acid solution was used to adjust the pH to about 4. Ethyl acetate was used for extraction 3 times (50 ml for each time). The organic layer was collected, washed once with 50 ml of saturated brine, dried over anhydrous sodium sulphate, and concentrated to obtain a pale yellow oil, which was directly used in the next step without purification, with a yield of >100%.

4) Synthesis of Compound 15

The crude product of the above-mentioned compound 13 was dissolved with 40 ml of DMF, and then added with 2.68 g (2 eq) of imidazole, followed by portion-wise addition of TBS-Cl; after that, stirring was performed at room temperature for 12 h until the reaction of raw materials was completed. 50 ml of water and 50 ml of ethyl acetate were added and stirred. The organic layer was separated, and the aqueous layer was extracted twice with ethyl acetate (50 ml for each time). The organic layer was collected, dried over anhydrous sodium sulphate, filtered and concentrated to obtain a pale yellow oil, which was subjected to column chromatography over silica gel (elution: PE:EA=5:1) to obtain 4.5 g of oil, with a yield of about 46.6% for two steps.

5) Synthesis of Compound 10

Compound 14, HOSu (1.23 g, 1.15 eq), DCC (2.23 g, 1.15 eq) and 50 ml of THF were sequentially added to a 250 ml single necked flask, and stirred at room temperature for 6 h under nitrogen. After the reaction was completed, 50 ml of water and 50 ml of ethyl acetate were added and stirred for 10 min, and then the organic layer was separated. The aqueous layer was then extracted twice with ethyl acetate (50 ml for each time) and the organic layer was combined, dried over anhydrous sodium sulphate, filtered and concentrated to obtain a pale yellow oil, which was purified by preparative liquid chromatography so as to obtain about 3.24 g of white foamy solid with a yield of 60%. $^1$H-NMR (400 MHz, DMSO-$d^6$): 0.08 (s, 6H), 0.86 (s, 9H), 0.98 (d, 3H, J=8.0 Hz), 1.06 (d, 3H, J=5.6), 1.95 (t, J=10.8), 2.83 (s, 4H), 4.21 (dd, 1H, J=16.8 Hz, 8.0 Hz), 4.34 (dd, 1H, J=12 Hz, 4 Hz), 4.67-4.73 (m, 1H), 7.31 (d, 2H, J=8.0 Hz), 7.34-7.46 (m, 2H), 7.70-7.76 (m, 2H), 7.89 (t, 2H, J=12.0), 8.24 (d, 1H, J=8.8 Hz); MS: 581.34[M+H]

6) Synthesis of Compound 11

0.5 g of compound 09 was dissolved with 1.5 ml of dry DMF, and then compound 10 (701 mg, 2 eq) was added. pH was adjusted to 8-9 with DIPEA; under nitrogen, the reaction was performed for 5 h at room temperature and monitored by HPLC until the reaction of raw material 09 was substantially completed. The product was directly used in the next step without a post-treatment.

7) Synthesis of Compound 12

0.3 ml (20%) of piperidine was added to the above-mentioned reaction liquid; the reaction was stirred for 2 hours at room temperature and stopped until the reaction of the raw materials was completed (monitored by HPLC). Preparative liquid chromatography was used for purification (neutral, acetonitrile/pure aquatic system) to collect a target peak; after the removal of acetonitrile under reduced pressure, 277 mg of white powdered solid was obtained by lyophilization, with a yield of about 42.8% for two steps. MS: $[M+H]^+$ 1071.5120.

8) Synthesis of Compound 13

270 mg of compound 12 was dissolved with dry DMF. EDCI (96.6 mg, 2 eq); HOBT (170 mg, 5 eq) and DIPEA (0.22 ml, 5 eq) were added, and stirred for 4 h at room temperature until the reaction was completed (monitored by HPLC). Preparative liquid chromatography was used for purification (neutral, acetonitrile/pure aquatic system) to collect a target peak; after the removal of acetonitrile under reduced pressure, about 136.4 mg of white powdered solid was obtained by lyophilization, with a yield of 51.4% and MS: $[M+H]^+$ 1053.4908.

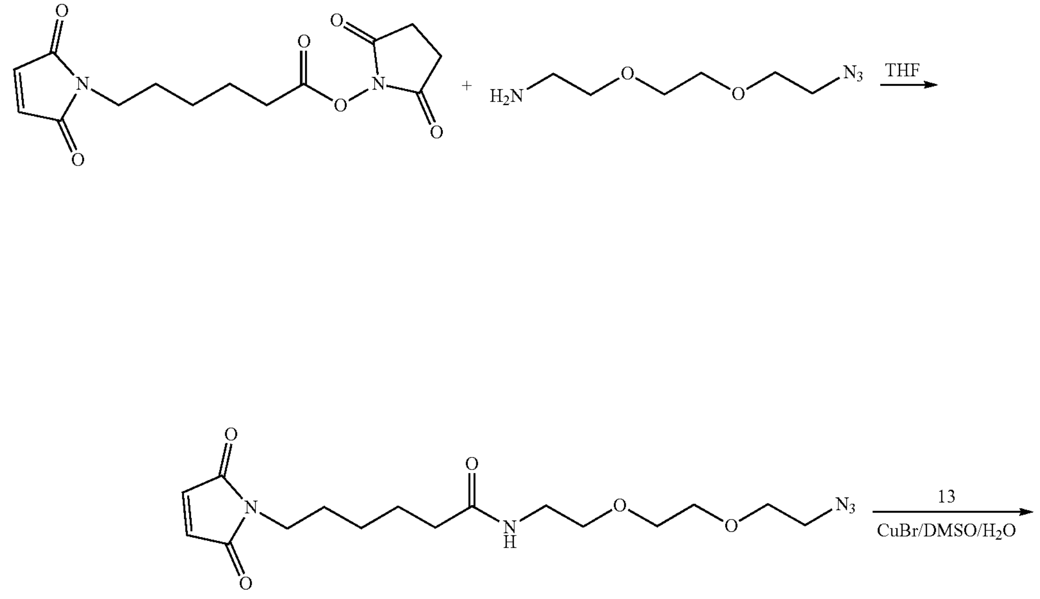

16

-continued

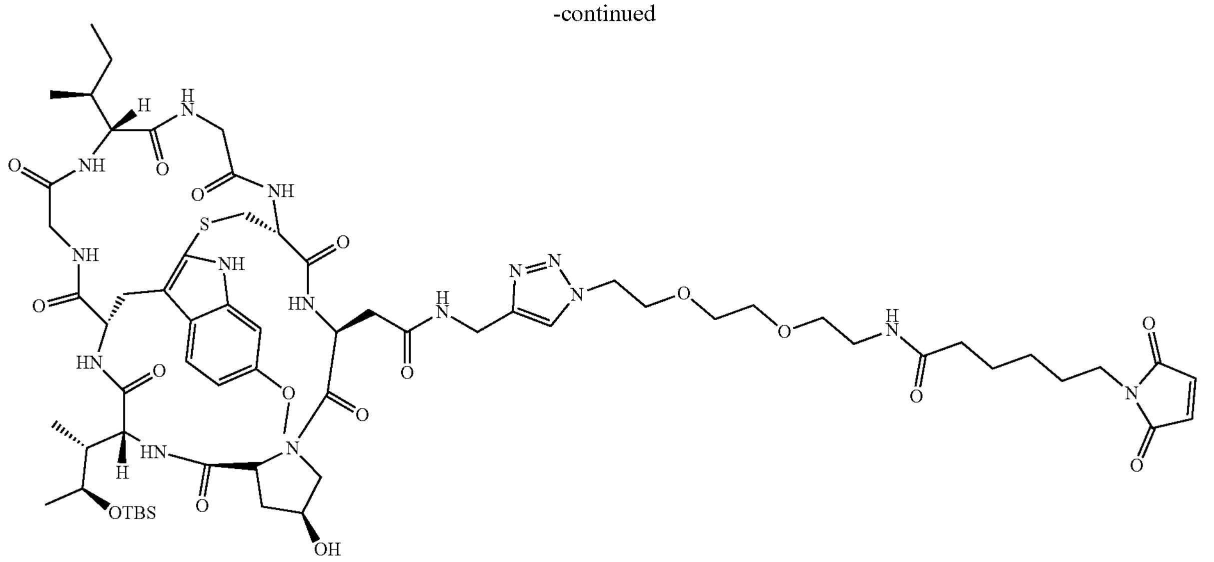

17

5% TFA/methanol

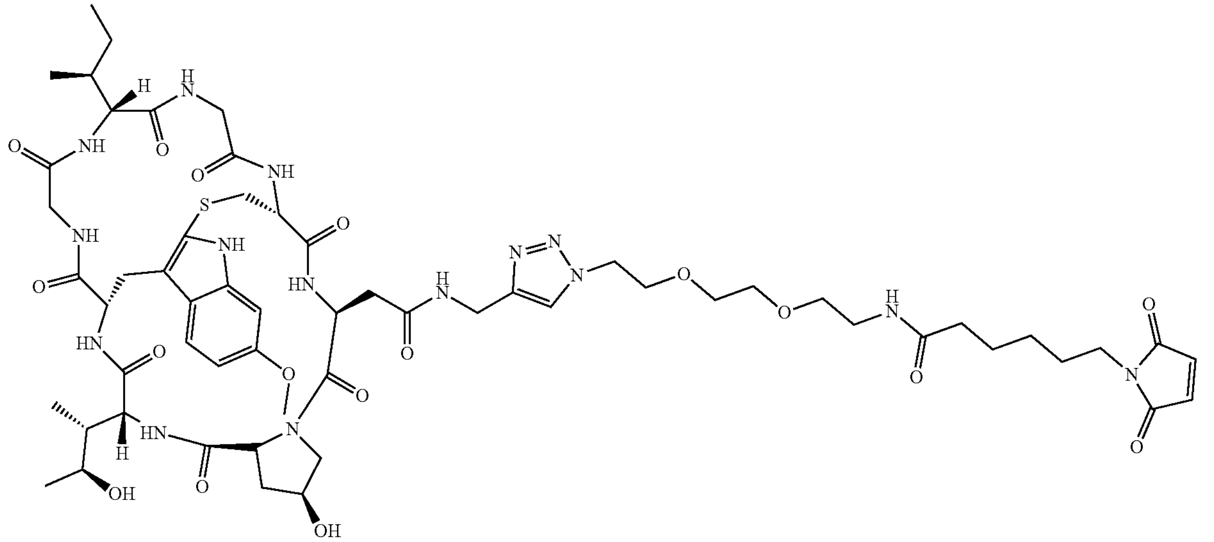

ama-0301

9) Synthesis of Compound 16

1 g of N-Succinimidyl 6-maleimidohexanoate was dissolved with 10 ml of tetrahydrofuran, and then 0.678 g of 2-[2-(2-azidoethoxy)ethoxy]ethylamine (1.2 eq) was added; stirring was performed at room temperature for 4 h under nitrogen until the reaction was completed (monitored by TLC); after that, water was added and EA was used for extraction 3 times (10 ml for each time). The organic layer was combined, dried, concentrated and purified by column chromatography to obtain about 0.8 g of target product with a yield of 84%.

10) Synthesis of Compound 17

80 mg of compound 16 was dissolved with 5 ml of DMSO, added with compound 13(114.7 mg, 0.5 eq), 44.7 mg (1.5 eq) of copper bromide and 0.2 ml of purified water; stirring was performed for 3 h at room temperature under nitrogen until the reaction of compound 13 was completed (monitored by HPLC); purification was performed using preparative liquid chromatography to collect a target peak, and the organic solvent was removed by rotary evaporation; about 50.5 mg of white solid was obtained by lyophilization, with a yield of 32.6%. MS: $[M+H]^+$ 1420.7031

11) Synthesis of Compound Ama-0301

45 mg of compound 17 was added with 1 ml of 5% TFA/MeOH to achieve dissolved clarification. The reaction was conducted at room temperature for 1 hour under nitrogen. After the reaction of raw material 17 was completed (monitored by HPLC) and the solvent was blow-dried with nitrogen, purification was performed using preparative liquid chromatography, and the organic solvent was concentrated and removed to obtain 15.4 mg of white solid by lyophilization, with a yield of 37.2%. MS: $[M+H]^+$ 1306.6013

Example 2 Synthesis of Small Molecule Payload
Ama-0302
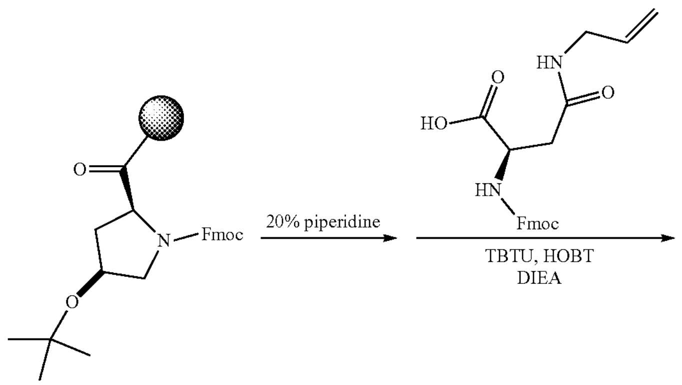
01
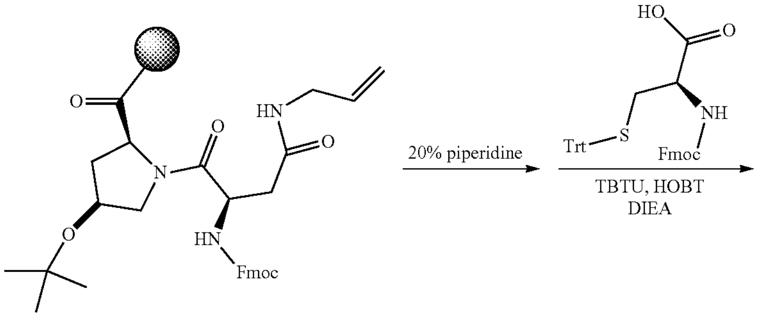
18
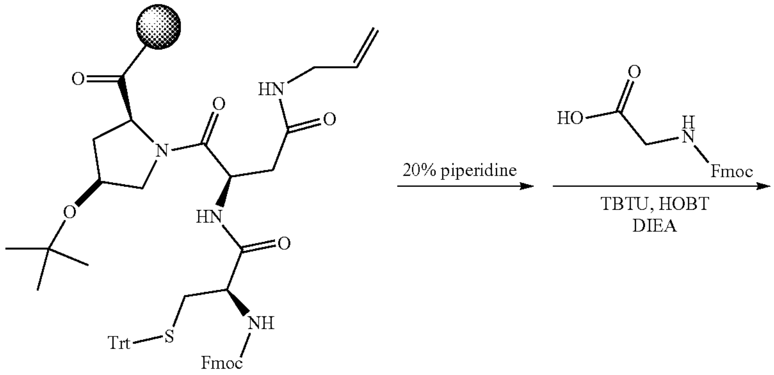
19
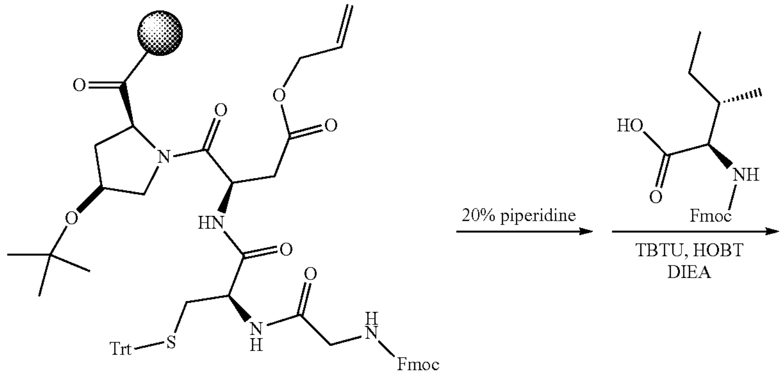
20

-continued
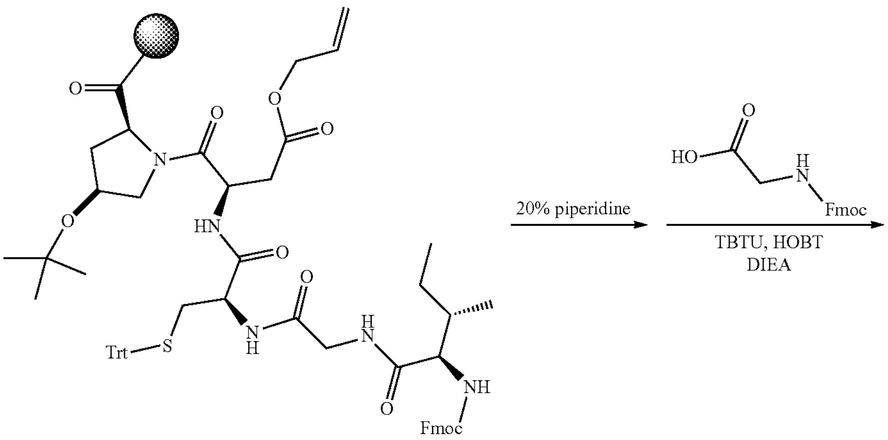
21
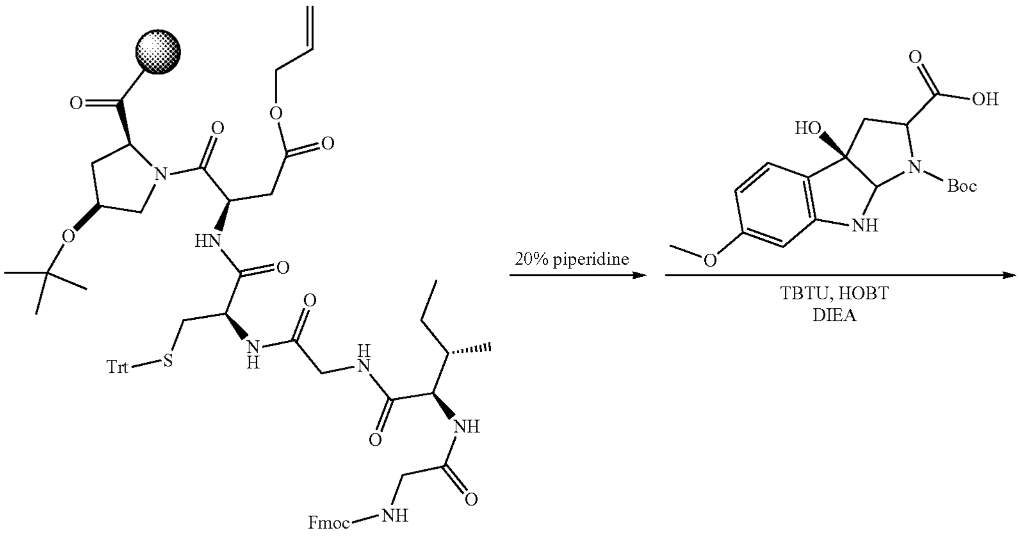
22

-continued
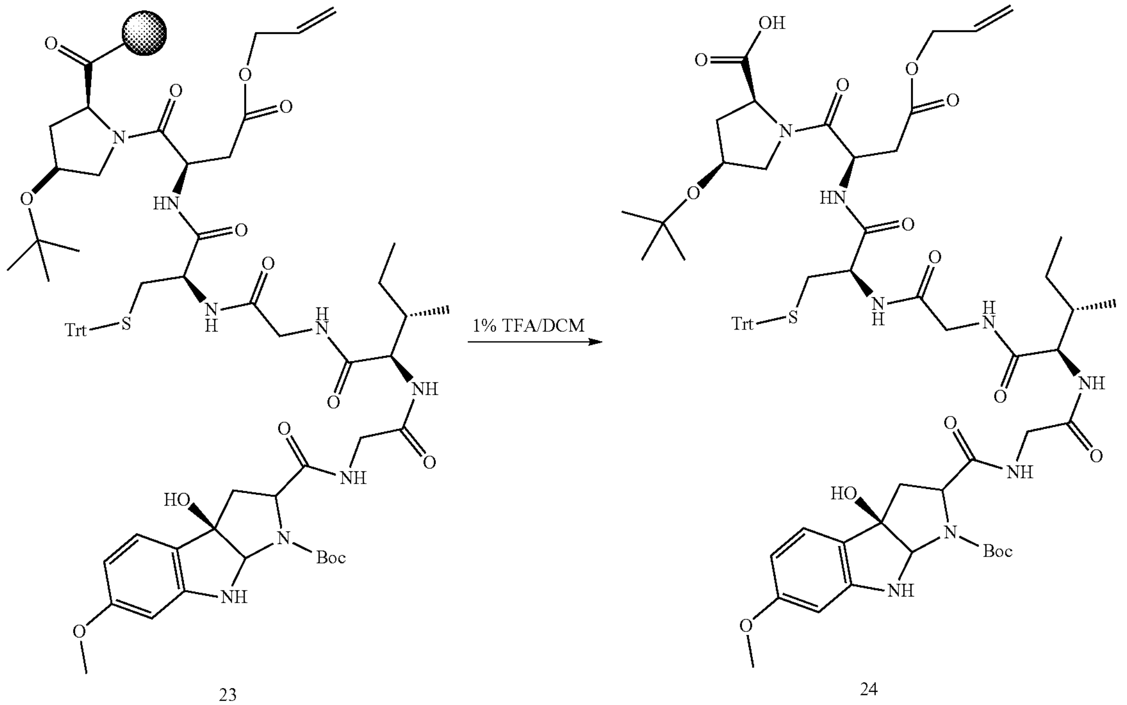
23
24
1) Solid Phase Synthesis of Key Intermediate 24
Reference was made to the synthesis of compound 08. After the crystallization with methyl tert-butyl ether, about 10.6 g of yellow-brown solid was obtained with a high purity of about 79.8%.
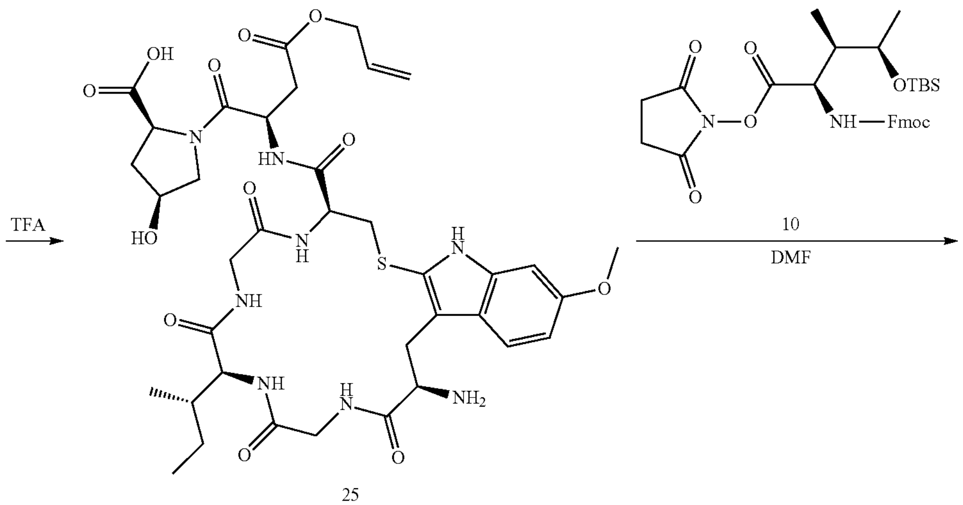
24
25
10

-continued
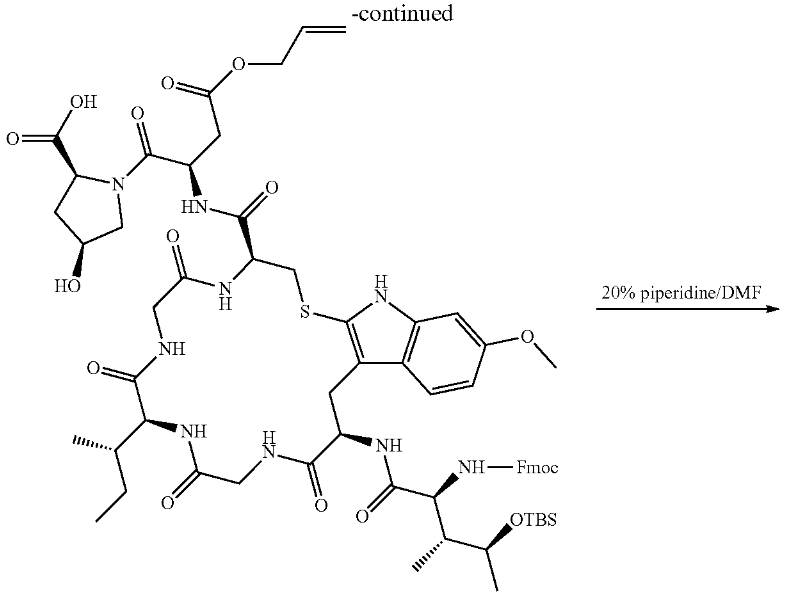
26
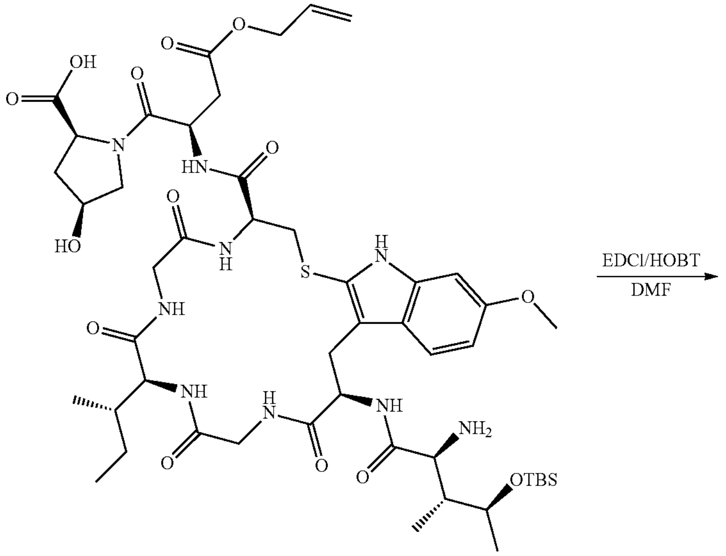
27

-continued
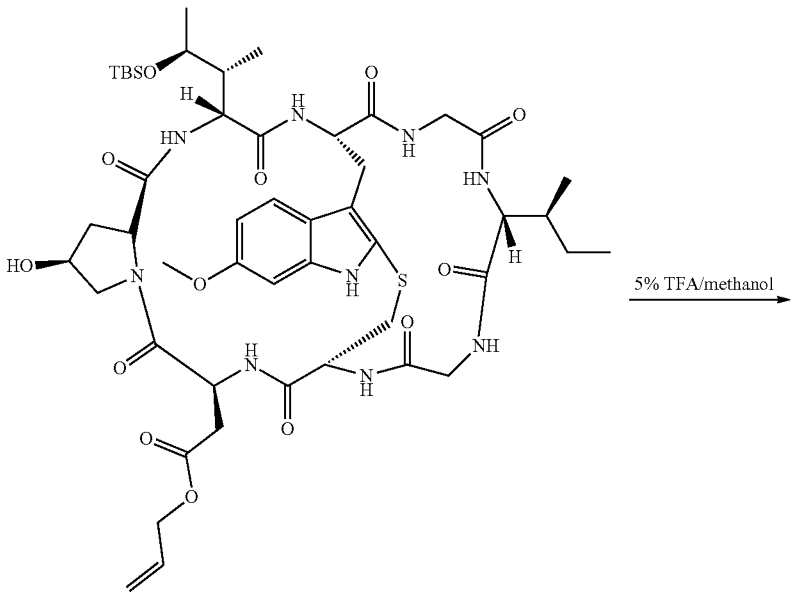
28
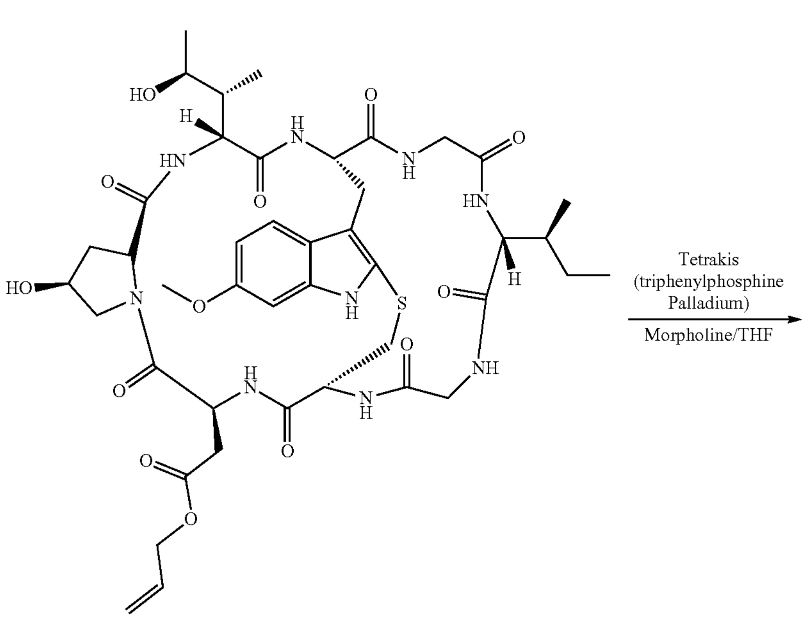
29

-continued

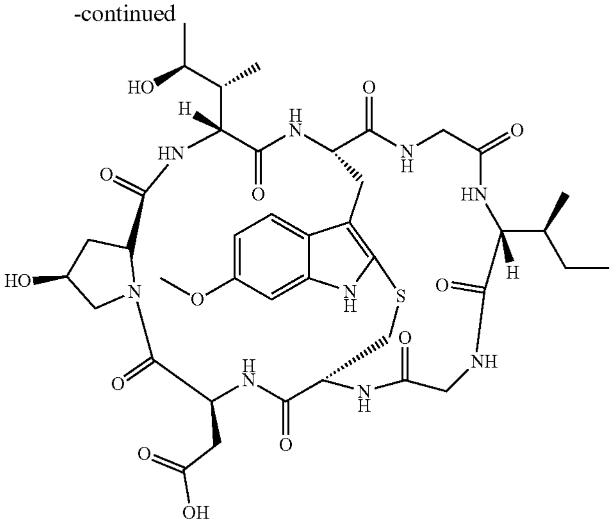

30

2) Synthesis of Compound 25

Reference was made to the synthesis of compound 09. The crude product of compound 24 was dissolved with 50 ml of TFA, and stirred at room temperature for 5 h under nitrogen until the reaction of the raw materials was completed with obvious main point, observed by high performance monitoring; purification was performed using preparative liquid chromatography to collect a target peak. After the organic solvent was removed under reduced pressure, 2.38 g of white solid was obtained by lyophilization. MS: $[M+H]^+$ 831.4251

3) Synthesis of Compound 26

Reference was made to the synthesis of compound 11. 1.0 g of raw material 25 was added, and about 820 mg of white solid was obtained by lyophilization, with a yield of 52.5%. MS: $[M+H]^+$ 1296.6431

4) Synthesis of Compound 27

Reference was made to the synthesis of compound 12. 800 mg of raw material 26 was added, and about 308.8 mg of white solid was obtained by lyophilization, with a yield of about 46.6%. MS: $[M+H]^+$ 1074.5184

5) Synthesis of Compound 28

Reference was made to the synthesis of compound 13. 300 mg of raw material 27 was added, and about 208.4 mg of white solid was obtained by lyophilization, with a yield of about 70.6%. MS: $[M+H]^+$ 1056.5243

6) Synthesis of Compound 29

100 mg of compound 28 was dissolved with 1 ml of 5% TFA in methanol solution; stirring was performed for 2 h at room temperature under nitrogen until the reaction of the raw materials was completed (monitored by high performance HPLC); purification was performed using preparative liquid chromatography to collect a target peak, and about 69.5 mg of pale yellow solid by lyophilization, with a yield of 77.9%. MS: $[M+H]^+$ 942.4571

7) Synthesis of Compound 30

50 mg of compound 29 was added to 10 ml of a reaction flask, and under nitrogen, 67.5 mg (1.1 eq) of tetrakis (triphenylphosphine palladium) was added. The air was replaced with nitrogen, and 5 ml of dry tetrahydrofuran and 0.1 ml of dry morpholine were added to a reaction flask via a syringe. The raw materials were dissolved and stirred for 12 h at room temperature until the reaction of the raw materials was completed (monitored by HPLC). Purification was performed using preparative liquid chromatography to collect a target peak, and about 35.2 mg of pale yellow solid was obtained by lyophilization, with a yield of 73.5%. MS: $[M+H]^+$ 902.4123

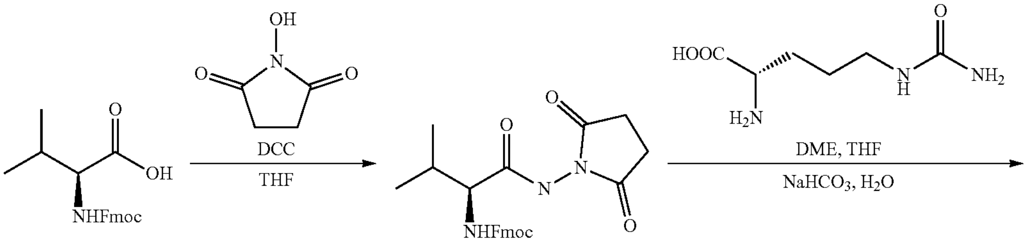

31

-continued
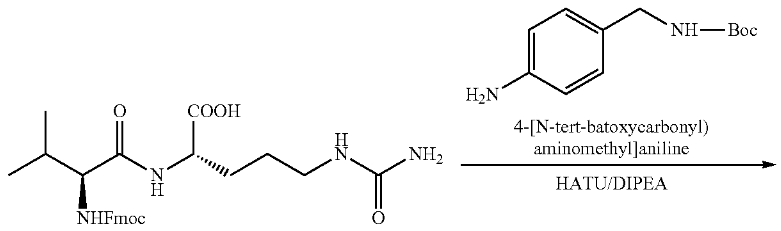
32
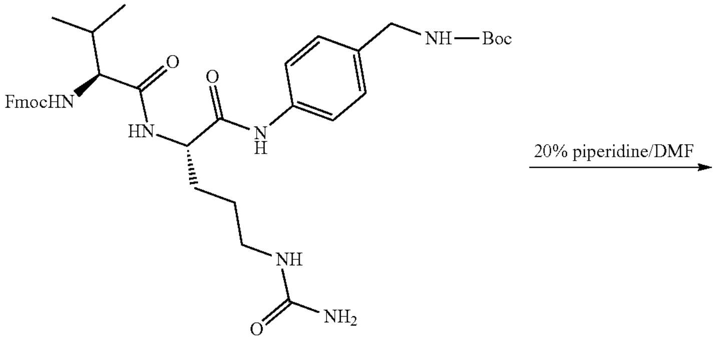
33
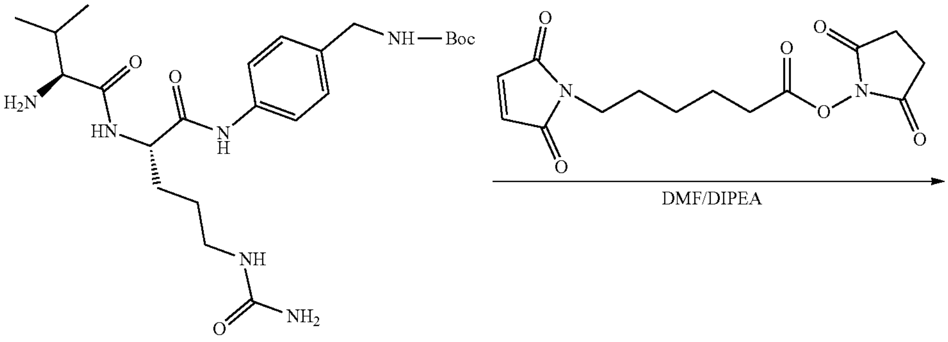
34
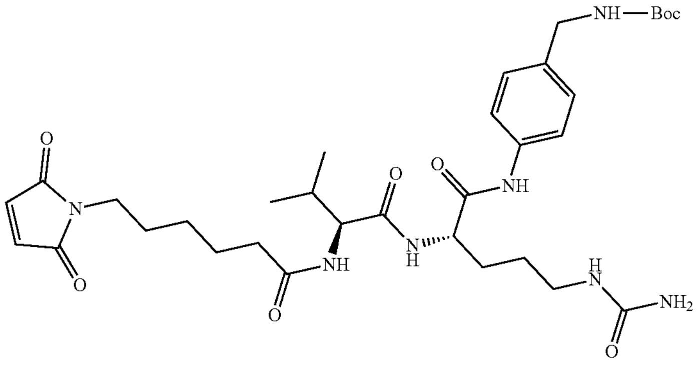
35

-continued

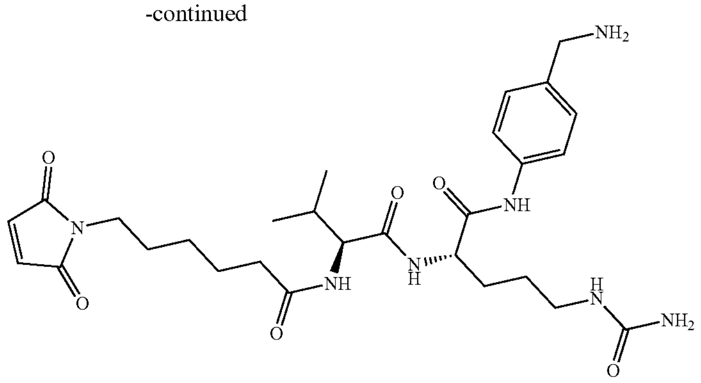

36

8) Synthesis of Compound 31

Fmoc-L-valine (20 g) and HoSu (7.46 g, 1.1 eq) were dissolved with 200 ml of THF; then the reaction flask was placed in an ice salt bath and cooled to 0° C. DCC condensing agent (14.6 g, 1.1 eq) was added slowly, and the reaction temperature was controlled at 0-5° C., with the addition being completed within 3 hours. The resultant was removed form ice bath, and stirred and reacted for 12 h. The reaction was stopped until the reaction of Fmoc-L-valine was completed (monitored by TLC). Suction filtration was performed under reduced pressure, and filter cake was washed with 100 ml of THF. The filtrate was subjected to rotational drying. The residue thereof was added with 100 ml of DCM, dissolved with stirring at 35° C., filtered to remove a little insoluble substance using an organic membrane filter, and then placed in an oil bath pan at 35° C. 100 ml of petroleum ether was added under stirring; crystallization was performed through 1 hour of natural cooling, and then 2 hours of cooling in an ice salt bath. Suction filtration was performed, and the solid was washed with petroleum ether, and dried in a vacuum oven at 40° C. to obtain 21.86 g of white powdered solid, with a yield of about 85%.

9) Synthesis of Compound 32

20 g of compound 31 was dissolved in 200 mL of THF as a solvent, and added with 9.64 g (1.2 eq) of L-citrulline; 1 M sodium carbonate was added to adjust pH to 8 to 9, and a dissolved clarification of the reaction was not achieved. The stirring was performed for 48 h at room temperature until the reaction was completed (monitored by TLC). Under an ice bath stirring, the reaction liquid was adjusted to a pH of 3-4 using citric acid aqueous solution and was extracted 3 times with isopropanol:EA=1:5 (40 ml of isopropanol+200 ml of EA). The organic phase was combined, dried over anhydrous sodium sulphate, filtered and subjected to rotational drying, followed by adding 200 ml of methyl tert-butyl ether and stirring for 2 hours; suction filtration was then performed to collect the filter cake, which was dried in a vacuum oven at 45° C. so as to obtain 18.6 g of white solid product, with a yield of about 81.7%.

10) Synthesis of Compound 33

18 g of compound 32 was added to a 500 mL reaction flask and dissolved with 200 mL DMF; then 8 g (1.0 eq) of 4-[(N-tert-butoxycarbonyl)aminomethyl]aniline, 20 g (1.5 eq) of HATU and DIPEA (18 mL, 3 eq) were added sequentially and stirred for 24 h at room temperature. After the reaction of the raw materials was completed (monitored by TLC), 200 mL of water and 200 mL of dichloromethane were added, and stirred for 10 min. Then the organic layer was separated, and washed twice with water (50 mL for each time). The organic layer was collected, dried over anhydrous sodium sulphate, and then filtered and concentrated to obtain a brown oil. 200 mL of methyl tert-butyl ether was added to the oil and stirred for 30 min; then the solid was washed out and filtered off, and the filter cake was washed twice with methyl tert-butyl ether (50 mL for each time). The filter cake was collected and dried in a vacuum oven at 50° C. to obtain 18.9 g of brown solid, with a yield of 74.4%.

11) Synthesis of Compound 34

15 g of compound 33 was added to a 250 mL reaction flask, to which 75 mL of 20% piperidine in DMF solution was added; stirring was performed for 1 h at room temperature until the reaction of the raw materials was completed (monitored by TLC). The solvent was distilled off under reduced pressure from oil pump, and then 200 mL of methyl tert-butyl ether was added and stirred for 2 h at room temperature. A brown solid was precipitated and filtered. The filter cake was washed twice with methyl tert-butyl ether (50 mL for each time), collected and dried in a vacuum oven at 50° C. to obtain 6.8 g of brown solid, with a yield of 66.4%.

12) Synthesis of Compound 35

1 g of compound 34 was dissolved with 10 mL of DMF, and then added with 773 mg of N-Succinimidyl 6-maleimidohexanoate (1.2 eq); stirring was performed for 5 h at room temperature until the reaction of the raw materials was completed (monitored by TLC). 10 mL of water and 20 mL of ethyl acetate were added to the reaction liquid and stirred for 10 min. The organic layer was then separated, dried over anhydrous sodium sulphate, filtered, concentrated and purified by column chromatography (petroleum ether:ethyl acetate=50:1) to obtain 956 mg of pale yellow foamy solid, with a yield of 68.3%.

13) Synthesis of Compound 36

30 mg of compound 35 was dissolved with 20% TFA in dichloromethane solution, and then stirring was performed for 2 h at room temperature until the reaction was completed (monitored by TLC). The solvent was removed by rotary evaporation under reduced pressure to obtain a crude product of compound 36 for later use, which was directly used in the next step without purification.

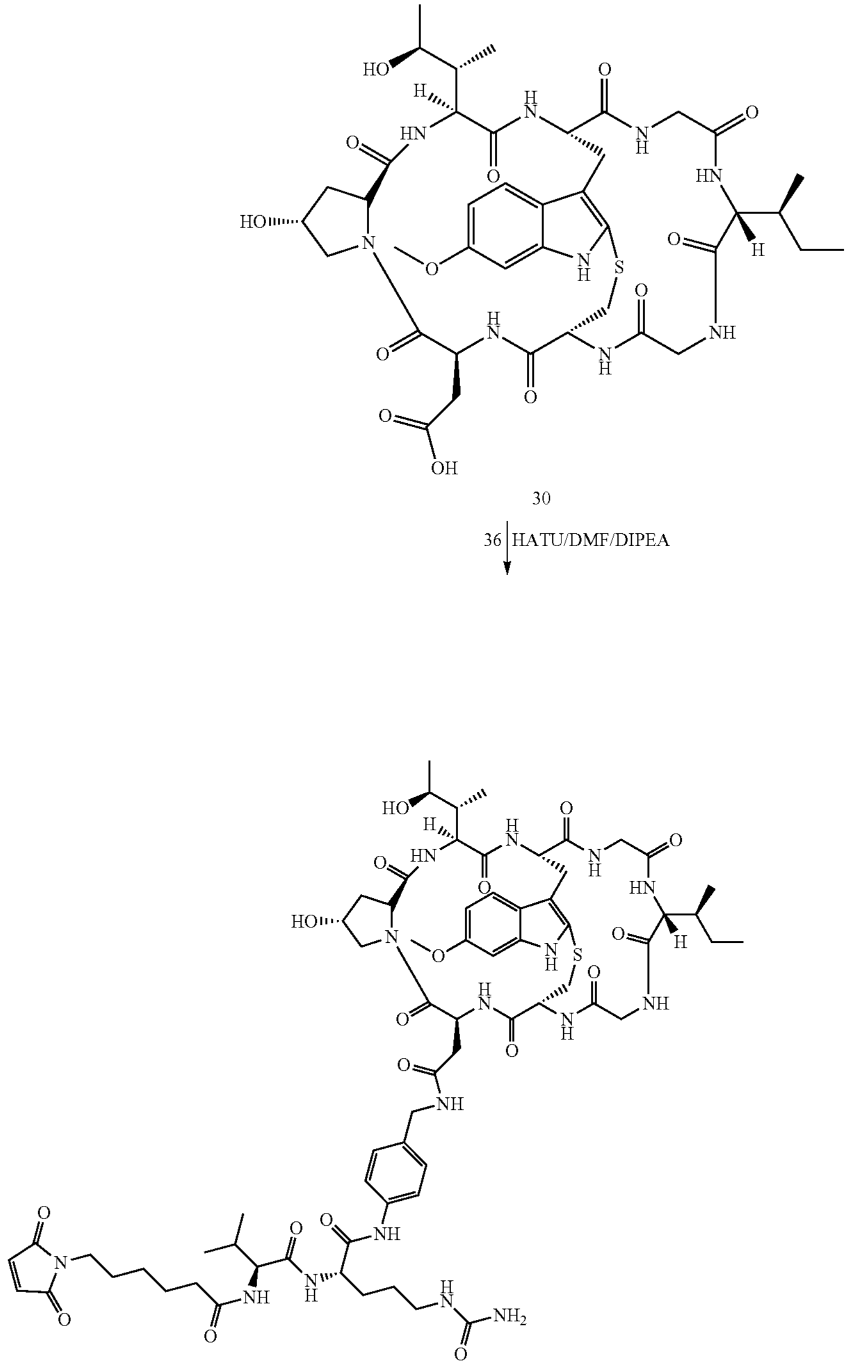

30 ama-0302

14) Synthesis of Ama-0302

The crude product of compound 36 (1.2 eq) obtained in the previous step was dissolved with 1 mL of DMF; 32.5 mg of compound 30 and 20.5 mg of HATU (1.5 eq) were then added, and the pH was adjusted to 8 to 9 with DIPEA; stirring was performed for 6 h at room temperature under nitrogen until the reaction of raw material 30 was completed (monitored by HPLC); purification was performed using preparative liquid chromatography to collect a target peak. After lyophilization, 15.3 mg of pale yellow solid was obtained, with a yield of 29.1%. MS: $[M+H]^+$ 1455.7011.

Example 3 Synthesis of Small Molecule Payload
Ama-0303
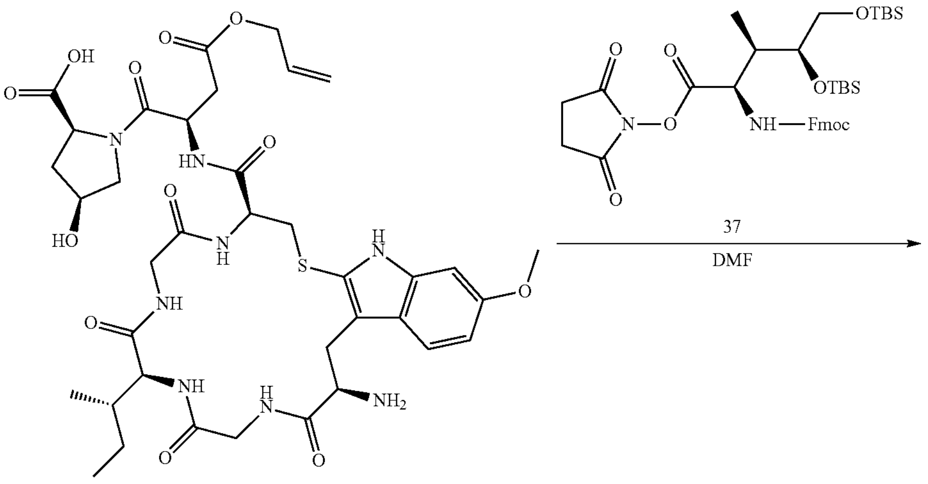
25
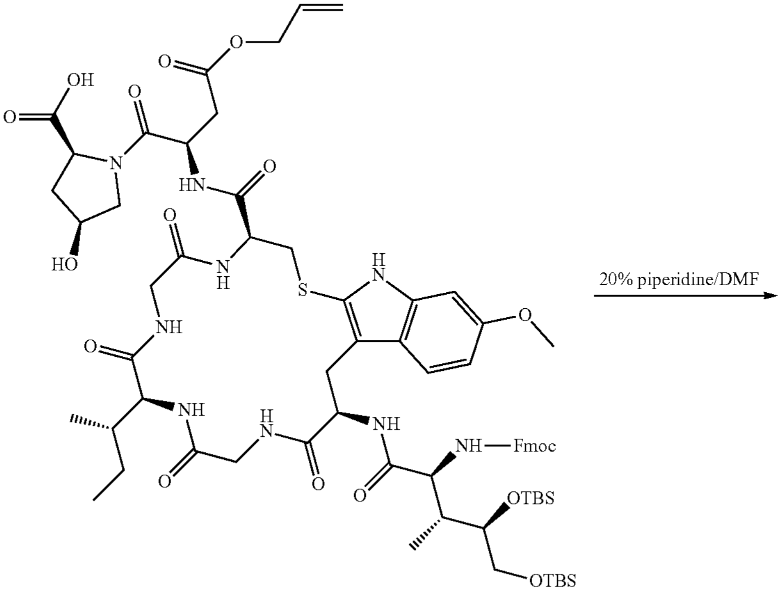
38

-continued
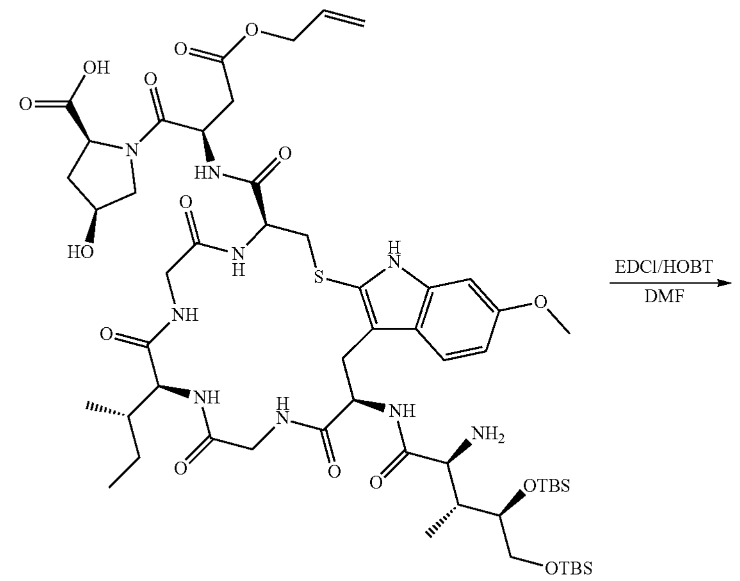
39
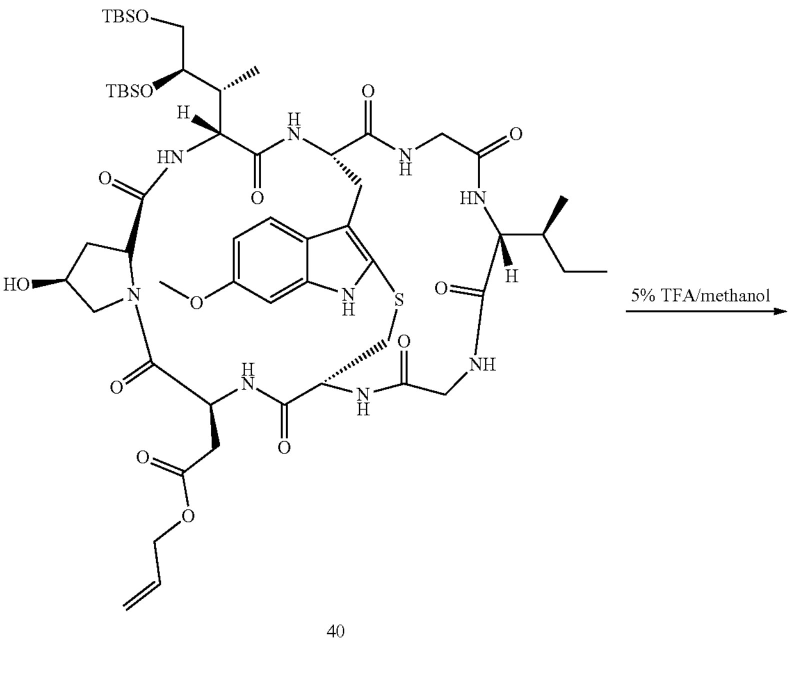
40

-continued

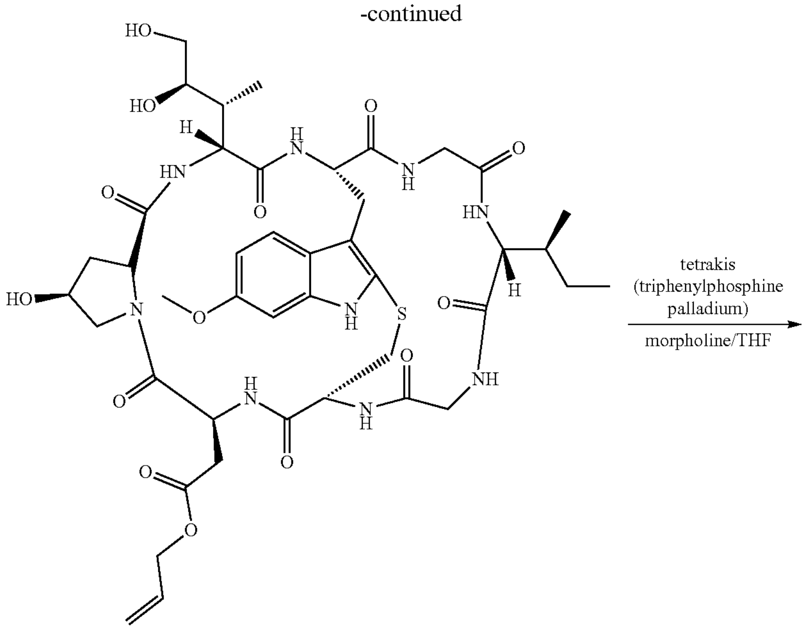

41

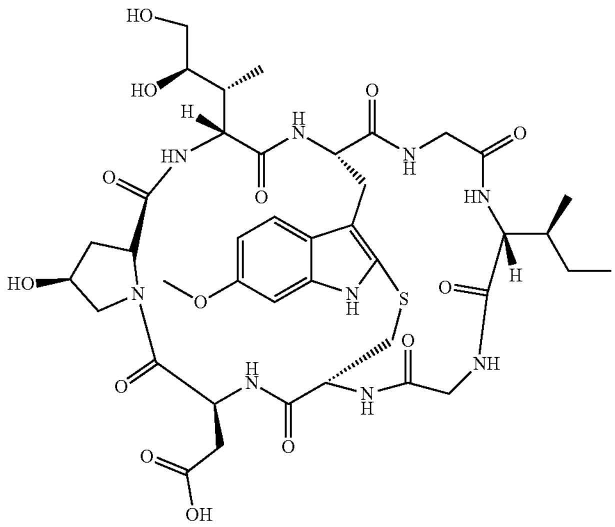

42

1) Synthesis of Compound 37

Reference is made to the synthesis method in J. Am. Chem. Soc. 2018, 140, 6513-6517.

2) Synthesis of Compound 38

Reference is made to the synthesis of compound 11. After lyophilization, about 751.5 mg of target compound was obtained, with a yield of 56.8%. MS: $[M+H]^+$ 1426.6751

3) Synthesis of Compound 39

Reference is made to the synthesis of compound 12. 700 mg of compound 38 was added, and about 482.3 mg of white solid was obtained by lyophilization, with a yield of 81.6%. MS: $[M+H]^+$ 1205.6124

4) Synthesis of Compound 40

Reference is made to the synthesis of compound 13. 450 mg of compound 39 was added. After purification was performed using preparative liquid chromatography, about 384.2 mg of white solid was obtained by lyophilization, with a yield of 86.7%. $[M+H]^+$ 1186.6012

5) Synthesis of Compound 41

Reference is made to the synthesis of compound 29. 100 mg of compound 40 was added; after purification was performed using preparative liquid chromatography, about 54.2 mg of white solid was obtained by lyophilization, with a yield of about 67.2%. $[M+H]^+$ 958.4250.

6) Synthesis of Compound 42

Reference is made to the synthesis of compound 30. 50 mg of compound 41 was added; after purification was performed using preparative liquid chromatography, about 28.6 mg of white solid was obtained by lyophilization of the target peak, with a yield of 59.7%. $[M+H]^+$ 918.4413

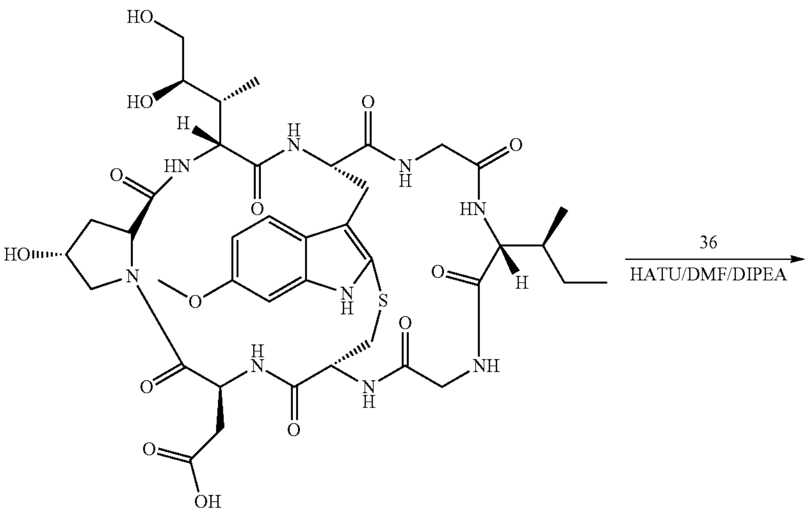
42
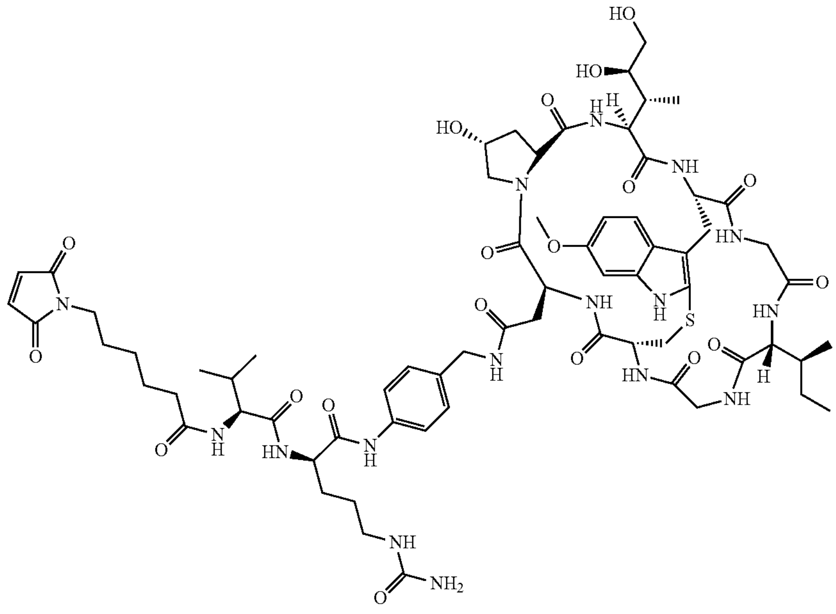
ama-0303
7) Synthesis of Compound Ama-0303
Reference was made to the synthesis of compound ama-0302. 25 mg of compound 42 was added; after purification was performed using preparative liquid chromatography, about 15.2 mg of pale yellow solid was obtained by lyophilization, with a yield of 38%. $[M+H]^+$ 1471.6820

Example 4 Synthesis of Small Molecule Payload
Ama-0304
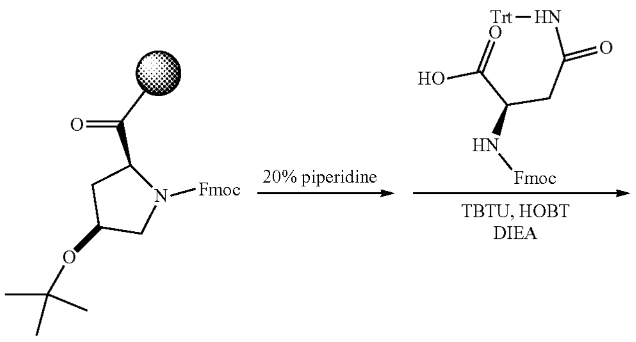
01
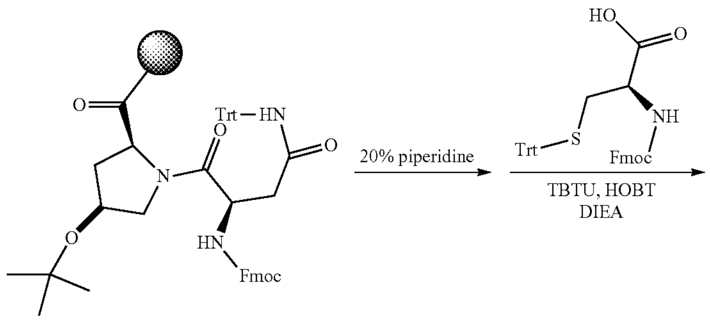
43
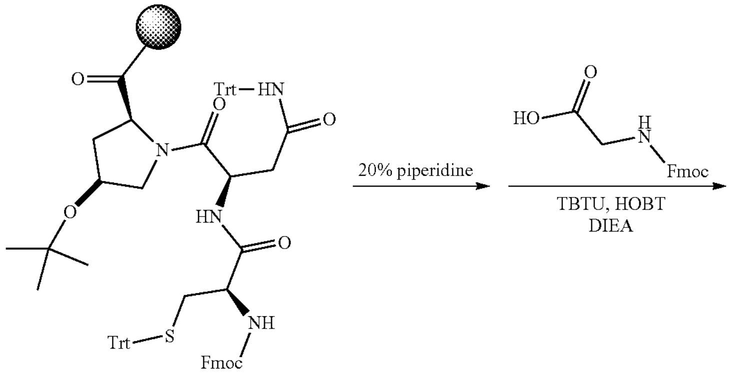
44
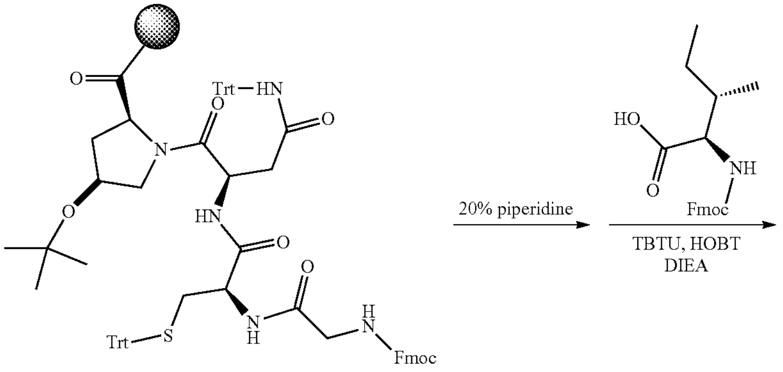
45

-continued
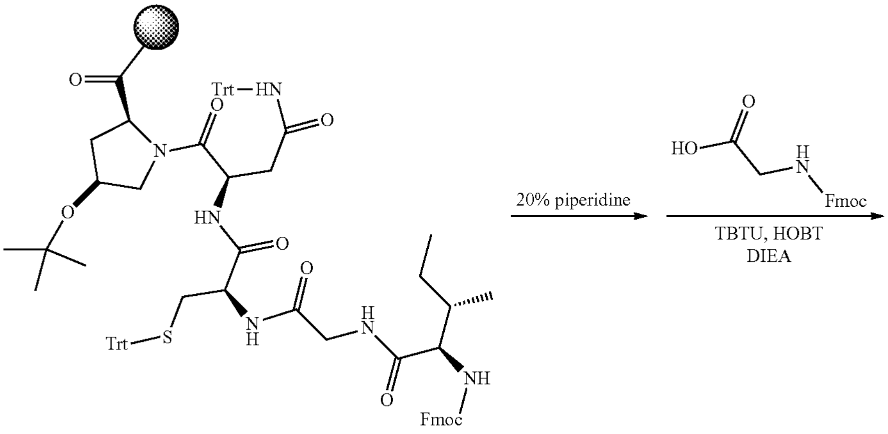
46
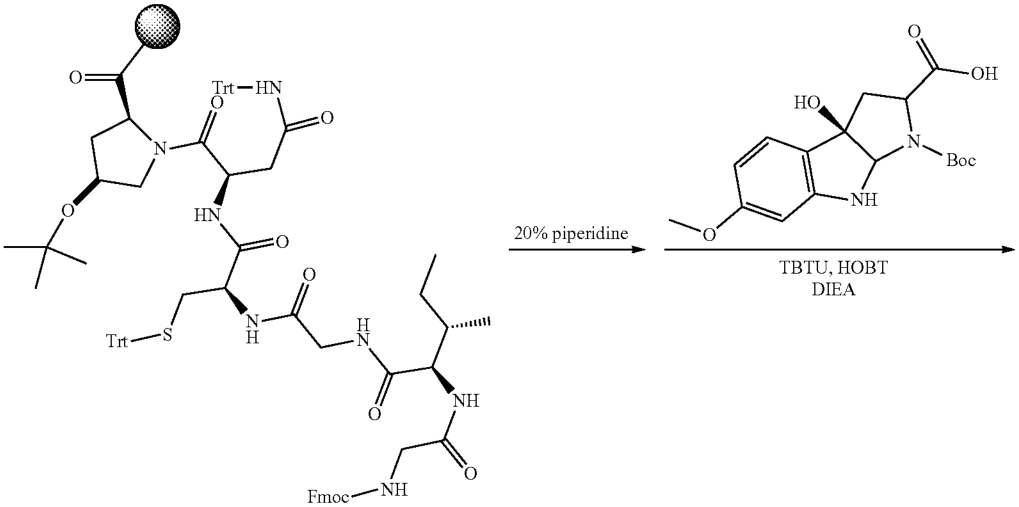
47

-continued
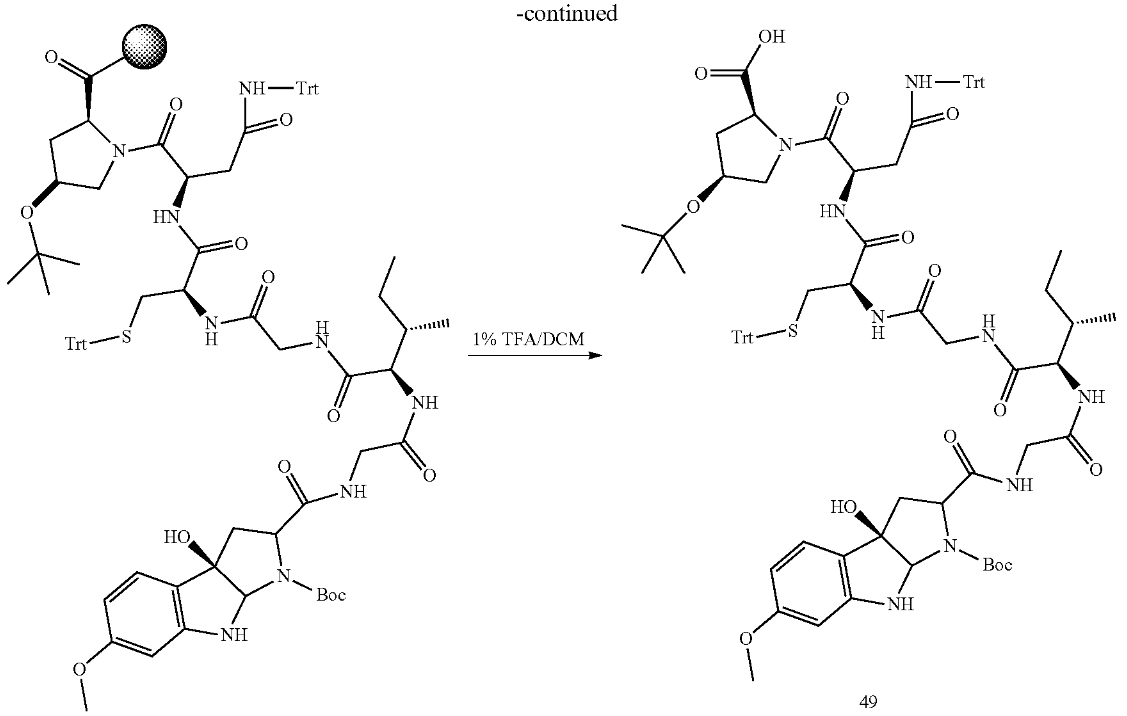
48
49
1) Synthesis of Compound 49
With regard to the synthesis method, reference was made to the synthesis of compound 08; about 2.4 g of crude product of compound 49 was obtained, with a purity of about 86.2%, which was directly used in the next step without purification.
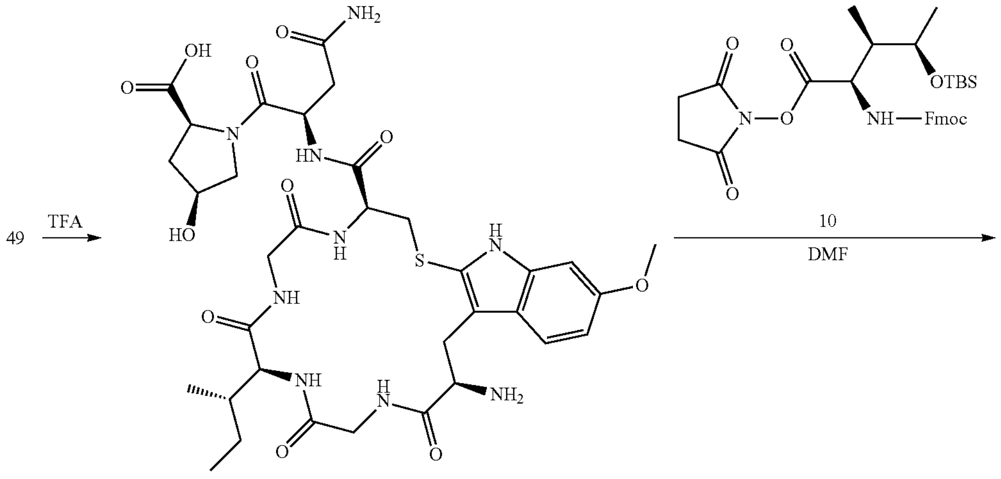
50

-continued
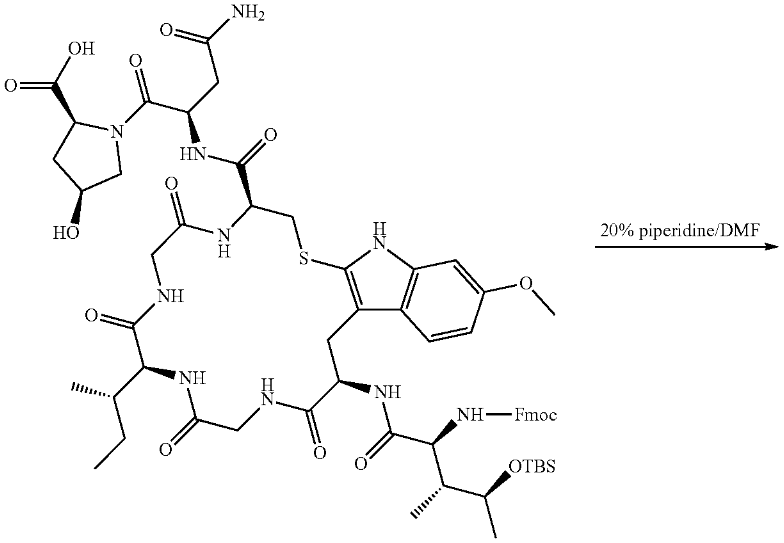
51
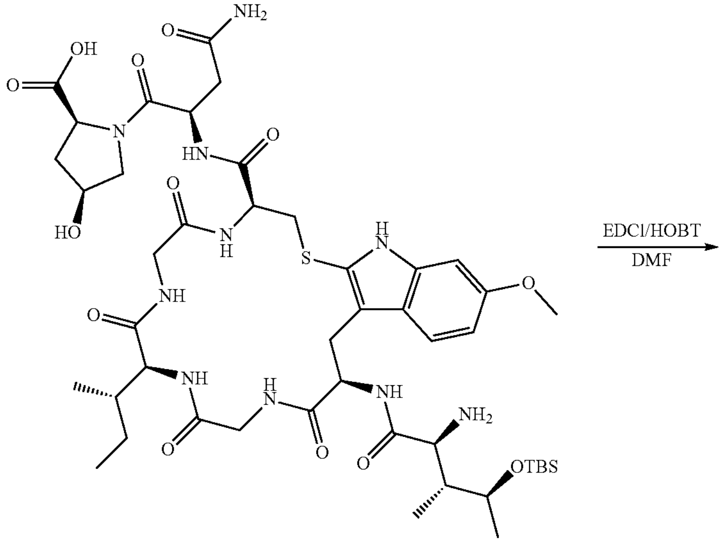
52
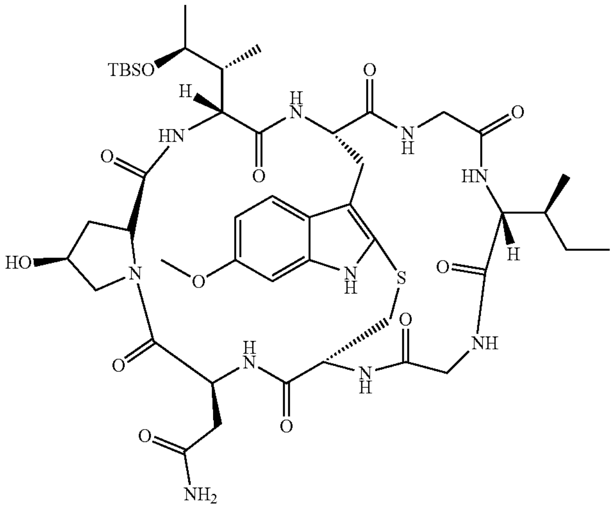
53

2) Synthesis of Compound 50

Reference was made to the synthesis of compound 09; after purification was performed using preparative liquid chromatography, about 1.1 g of target compound was obtained. $[M+H]^+$ 790.4126

3) Synthesis of Compound 51

Reference was made to the synthesis of compound 11. 500 mg of compound 50 was added; after purification was performed using preparative liquid chromatography, 341.5 mg of target compound was obtained, with a yield of 43%. $[M+H]^+$ 1255.6195

4) Synthesis of Compound 52

Reference was made to the synthesis of compound 12. 300 mg of compound 51 was added; after purification was performed using preparative liquid chromatography, about 186.4 mg of white solid was obtained by lyophilization of the target peak, with a yield of 75.5%. $[M+H]^+$ 1033.5013

5) Synthesis of Compound 53

Reference was made to the synthesis of compound 13. 150 mg of compound 52 was added; after purification was performed using preparative liquid chromatography, about 86.5 mg of white solid was obtained by lyophilization of the target peak, with a yield of 58.7%, $[M+H]^+$ 1015.5121

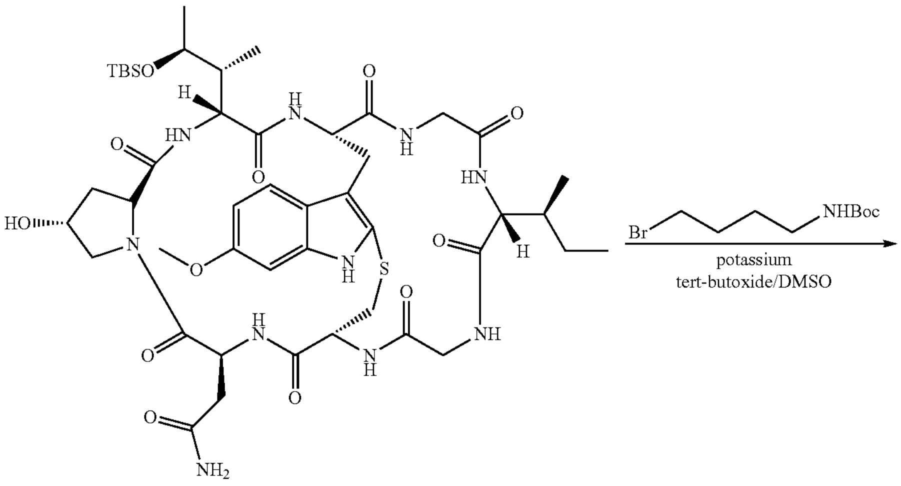

53

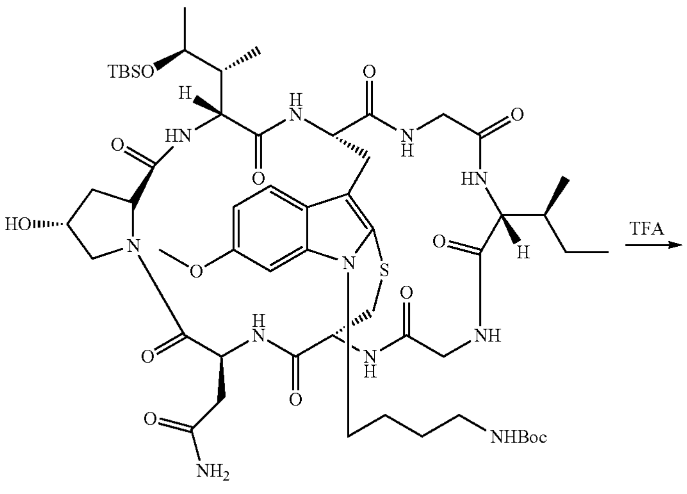

54

-continued

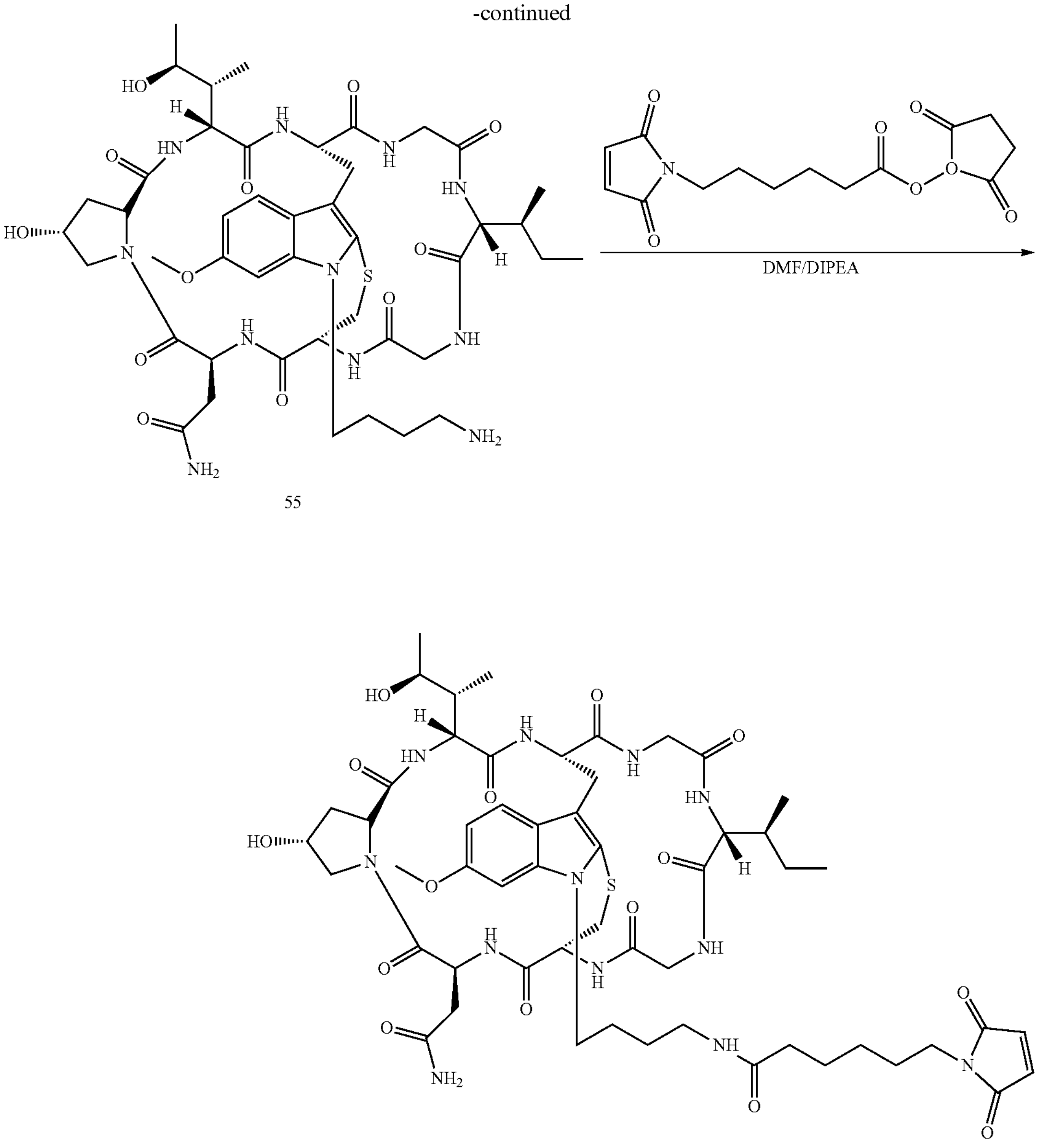

55 ama-0304

6) Synthesis of Compound 54

80 mg of compound 53 was dissolved with dry DMSO; 159 mg of tert-butyl N-(4-brombutyl) carbamic acid (8 eq) and 88 mg of potassium tert-butoxide (10 eq) were then added; the reaction was stirred for 12 h at room temperature and then 159 mg of tert-butyl N-(4-brombutyl)carbamic acid (8 eq) and 88 mg of potassium tert-butoxide (10 eq) were added. The reaction was stirred for another 24 h at room temperature until the raw materials disappeared (monitored by HPLC); purification was performed using preparative liquid chromatography to collect a target peak; and 18.2 mg was obtained, with a yield of 19.5%. $[M+H]^+$ 1186.6137.

7) Synthesis of Compound 55

18.2 mg of compound 54 obtained as above was dissolved with 0.1 mL of trifluoroacetic acid, and stirred for 30 min at room temperature. 2 mL of dichloromethane was added; after stirring same homogeneously, the solvent was removed by rotary evaporation under reduced pressure, and the resultant was retained for later use.

8) Synthesis of Compound Ama-0304

The crude product of compound 55 obtained as above was dissolved with 1 mL of DMF, and then 9.5 mg of N-Succinimidyl 6-maleimidohexanoate (2 eq) was added. The pH was adjusted to 8 to 9 with DIPEA; under nitrogen, stirring was performed for 5 h at room temperature until the reaction of the raw materials was completed (monitored by HPLC); purification was performed using preparative liquid chromatography to collect a target peak. After the organic solvent was removed by rotary evaporation, 10.4 mg of off-white solid was obtained by lyophilization, with a yield of 53%. $[M+H]^+$ 1279.6537.

Example 5 Synthesis of Small Molecule Payload
Ama-0305
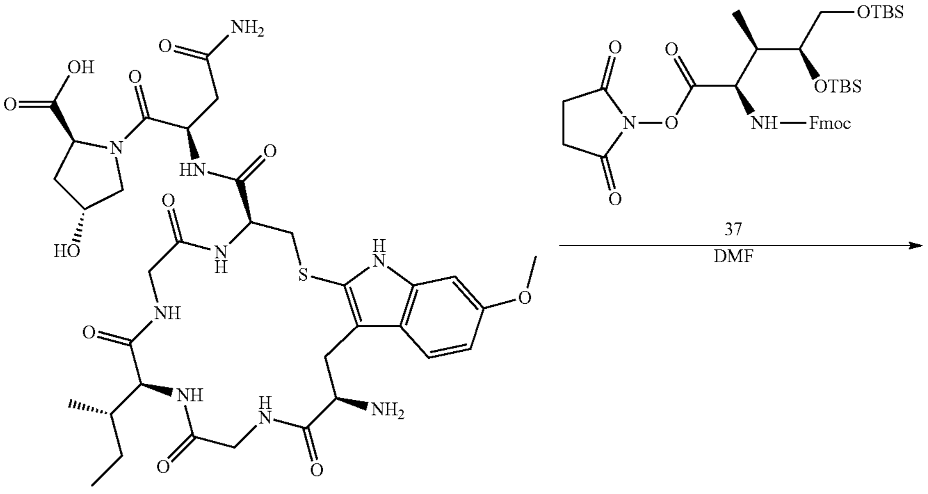
50
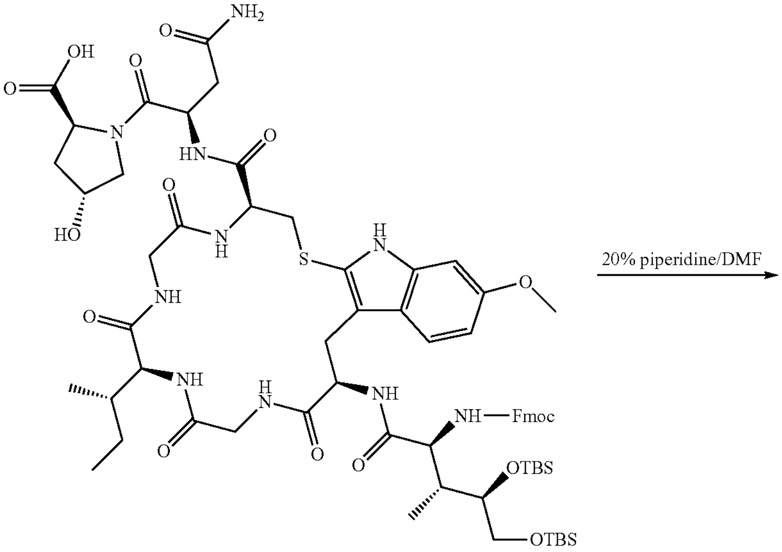
56

-continued
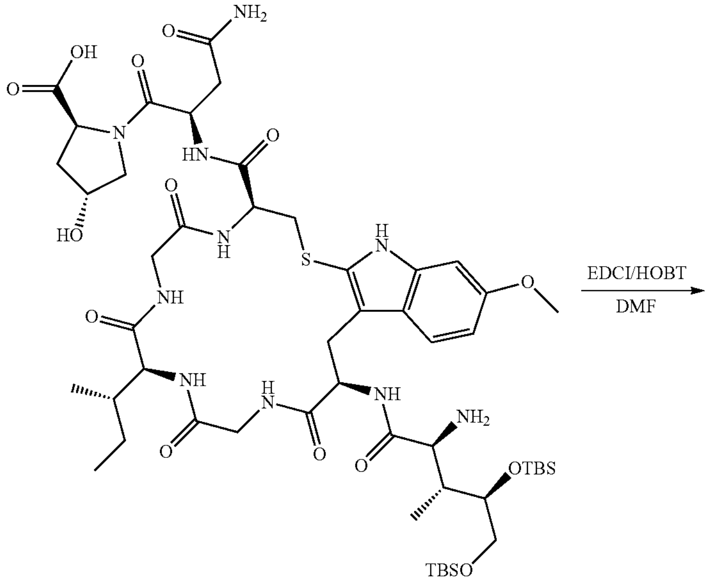
57
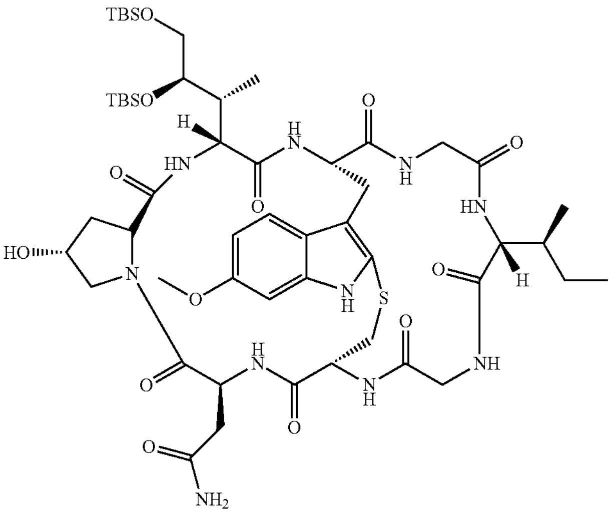
58
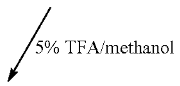

-continued

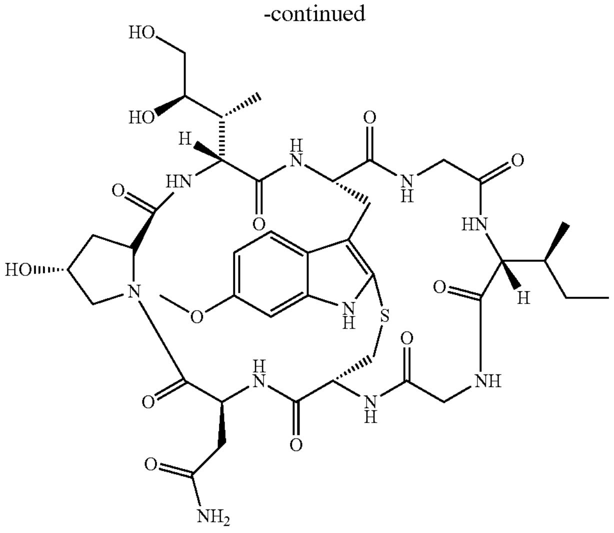

59

1) Synthesis of Compound 56

Reference was made to the synthesis of compound 11. 200 mg of raw material 50 was added, and about 211.3 mg of white solid was obtained by lyophilization, with a yield of 60.2%. $[M+H]^+$ 1385.6713.

2) Synthesis of Compound 57

Reference was made to the synthesis of compound 12. 200 mg of raw material 56 was added, and about 114.8 mg of white solid was obtained by lyophilization, with a yield of 68.3%. $[M+H]^+$ 1163.5793.

3) Synthesis of Compound 58

Reference was made to the synthesis of compound 13. 110 mg of raw material 57 was added, and about 72.5 mg of off-white solid was obtained by lyophilization, with a yield of 66.9%. $[M+H]^+$ 1145.5901.

4) Synthesis of Compound 59

About 70 mg of compound 58 obtained as above was dissolved with 0.5 mL of TFA in methanol solution; stirring was then performed for 1 h at room temperature until the reaction of the raw materials was completed (monitored by HPLC); purification was performed using preparative liquid chromatography to collect a target peak. After the organic solvent was removed by rotary evaporation, 45.7 mg of off-white solid was obtained by lyophilization, with a yield of 81.6%. $[M+H]^+$ 917.4013.

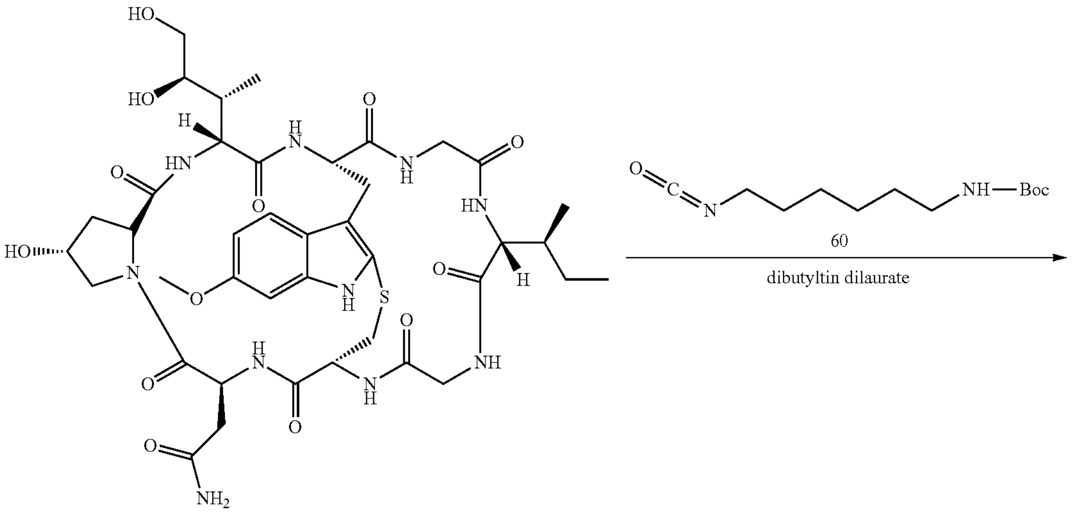

59

-continued
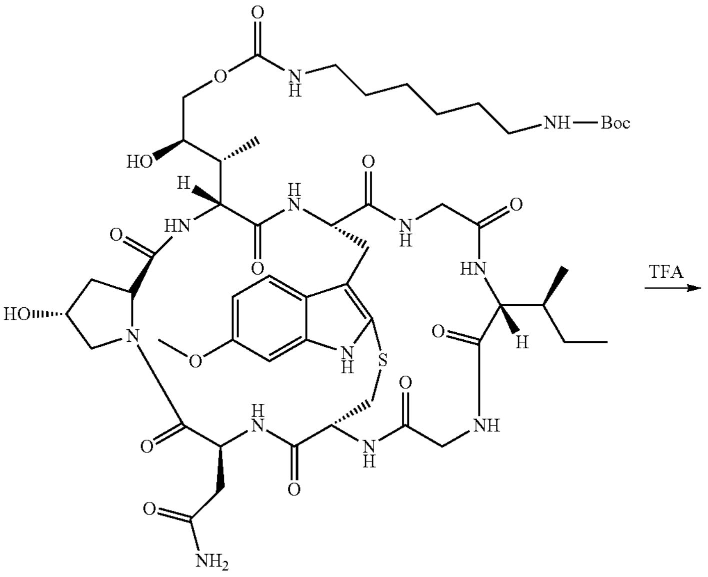
61
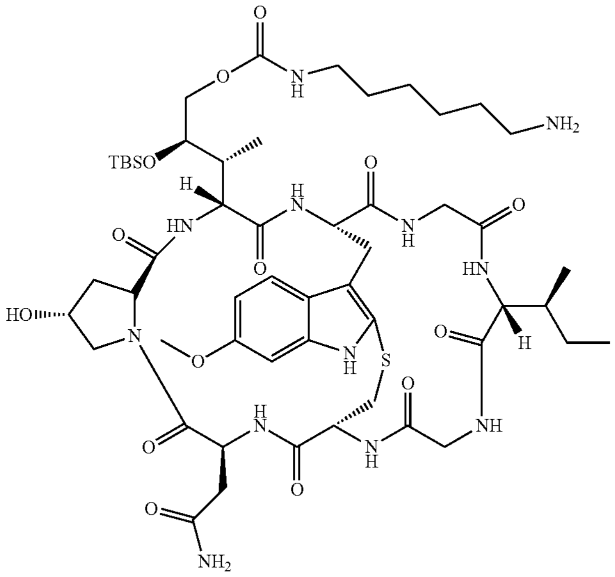
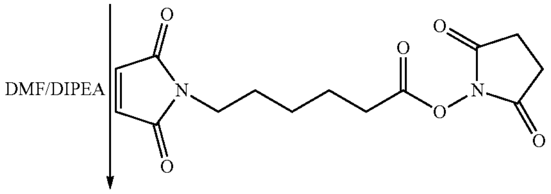

-continued

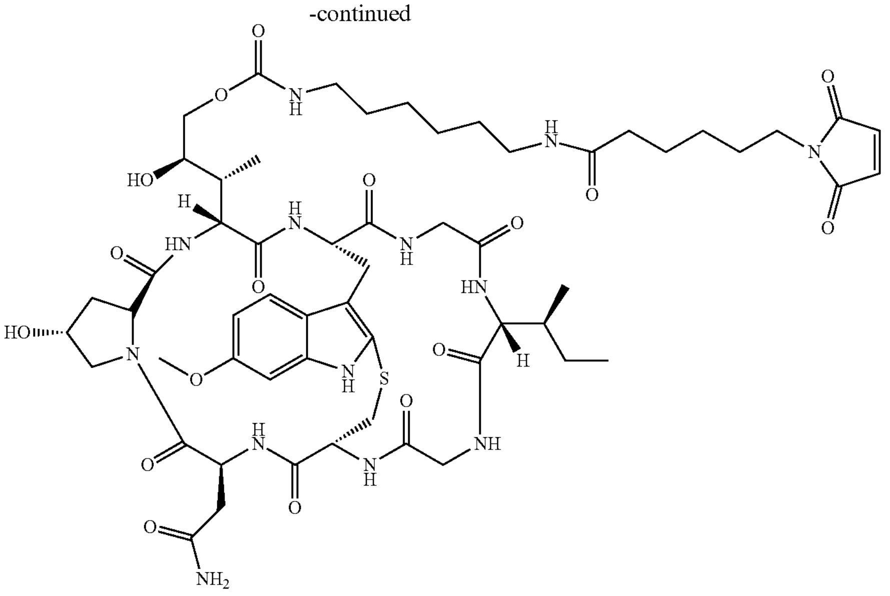

ama-03225

5) Synthesis of Compound 60

Reference is made to the method in patent WO2012041504

6) Synthesis of Compound 61

About 42 mg of raw material 59 was dissolved with 1 mL of dry DMF; 22 mg of compound 60 (2 eq) and 58 mg of dibutyltin dilaurate were then added; after that, stirring was performed for 24 h at room temperature under nitrogen. 22 mg of compound 60 (2 eq) was further added and stirring was continued for 52 h at room temperature until raw material 59 disappeared (monitored by HPLC). 0.2 mL of methanol was added to the above-mentioned reaction liquid to stop the reaction; purification was performed using preparative liquid chromatography to collect the target peak. The organic solvent was removed by rotary evaporation, and about 9.6 mg of pale yellow solid was obtained by lyophilization, with a yield of 18.1%. $[M+H]^+$ 1159.5703.

7) Synthesis of Compound 62

9.6 mg of compound 61 obtained as above was dissolved with 0.1 mL of trifluoroacetic acid, and stirred for 30 min at room temperature. 2 mL of dichloromethane was added; after stirring same homogeneously, the solvent was removed by rotary evaporation under reduced pressure, and the resultant was retained for later use, directly in the next step without purification.

8) Synthesis of Compound Ama-0305

Compound 62 obtained as above was dissolved with 1 mL of dry DMF, and then 5.1 mg of N-Succinimidyl 6-maleimidohexanoate (2 eq) was added; under nitrogen, stirring was performed for 5 h at room temperature until the reaction of the raw materials was completed (monitored by HPLC); purification was performed using preparative liquid chromatography to collect a main peak; after drying with nitrogen gas, 4.6 mg of off-white solid was obtained, with a yield of 44.4%. $[M+H]^+$ 1252.6091.

Example 6 Preparation of Antibody-Drug Conjugate

1) General Conjugation Method:

After preliminary purification, the antibody molecules with a monomer yield of more than 95% were subjected to a medium change and added to a phosphate buffer solution containing EDTA through an ultrafiltration centrifuge tube, with a concentration of 10 mg/mL. TCEP in an amount of 10 times the mole number of antibody molecules was added and reacted at room temperature for 2 h. The resultant was subjected to a medium change and added to a phosphate buffer solution at pH 6.5 through an ultrafiltration centrifuge tube; then DHAA in an amount of 10 times the mole number of antibody molecules was added and reacted at room temperature for 2 h. Then payload in an amount of 3 times the mole number of antibody molecules was added and reacted at room temperature for 4 h. After the completion of the reaction, the resultant was subjected to a medium change and added to PBS through an ultrafiltration centrifuge tube having a molecular weight cut-off of 30 KDa, and the uncoupled payload was removed.

2) Detection of Antibody-Drug Coupled DAR

Detection Conditions for Monomer Yield:

The samples were centrifuged at 14000 rpm for 5 minutes, and the supernatant was used for injection analysis.

- Instrument: Waters e2695 (2489 UV/Vis)
- Chromatographic column: TSKgel G3000SWXL (7.8×300 mm, 5 μm)
- Mobile phase: A: 50 mM PB, 300 mM NaCl, 200 mM Arg, 5% IPA, pH 6.5
- isocratic elution with mobile phase A for 30 min; flow rate: 0.714 mL/min; column temperature: 25° C.; and detection wavelength: 280 nm.

DAR detection conditions:

The samples were centrifuged at 14000 rpm for 5 minutes, and the supernatant was used for injection analysis.

Instrument: Waters H-class (TUV)

Chromatographic column: Proteomix HIC Butyl-NP5 (4.6×35 mm, 5 μm)

Mobile phase: A: 1.5 M ammonium sulphate, 0.025 M anhydrous sodium phosphate, pH 7.0

B: 0.025 M anhydrous sodium phosphate, 25% IPA, pH 7.0 chromatographic column equilibration with mobile phase A; gradient elution with mobile phase A and B; flow rate: 0.8 mL/min; column temperature: 25° C.; and detection wavelength: 214 nm.

3) Results

| Antibody-drug conjugate | Antibody | Payload | Monomer yield | DAR (theory 2.0) |
|---|---|---|---|---|
| Tras - 0301 | Trastuzumab | ama - 0301 | 96.1 | 1.81 |
| Tras - 0302 | Trastuzumab | ama - 0302 | 96.4 | 1.80 |
| Tras - 0303 | Trastuzumab | ama - 0303 | 96.8 | 1.84 |
| Tras - 0304 | Trastuzumab | ama - 0304 | 97.1 | 1.78 |
| Tras - 0305 | Trastuzumab | ama - 0305 | 96.7 | 1.76 |

4) Conclusion

After coupling ama-0301/ama-0302/ama-0303/ama-0304/ama-0305 with Trastuzumab, the coupling efficiency was higher and the monomer yield was better.

Example 7 Plasma Stability

1) Operations

A certain amount of ADC sample was added to human plasma from which human IgG was removed. Each ADC was repeated three times in triplicate, and placed in a 37° C. water bath for incubation. After incubating 72 h and 144 h respectively, ADC sample was taken out, and 100 ul of ProteinA resin (MabSelect SuRe™ LX Lot: #10221479 GE, washed with PBS) was added to each tube, which was subject to shaking using a vertical mixer for adsorbing 2 h; after washing and elution steps, ADC after incubation was obtained, and the ADC samples incubated for a specific time were detected by RP-HPLC.

2) Results

| Antibody-drug | DAR (theory 2.0) | |
|---|---|---|
| conjugate | 72 h | 144 h |
| Tras - 0301 | 1.78 | 1.76 |
| Tras - 0302 | 1.80 | 1.78 |
| Tras - 0303 | 1.83 | 1.82 |
| Tras - 0304 | 1.76 | 1.76 |
| Tras - 0305 | 1.74 | 1.72 |

3) Conclusion

In human plasma, each antibody-drug conjugate almost has no degradation at 3 and 6 days, and has a good stability.

Example 8 In Vitro Activity Test

1) Experiment Materials

Cells: from Cell Bank of Chinese Academy of Sciences

Tumor cell culture medium: Gibco

FBS: BIOWEST

2) Preparation of Culture Medium

Growth medium (with 10% FBS, Penicillin/streptomycin (100 U/mL))

Detection medium (with 1% FBS, Penicillin/streptomycin (100 U/mL))

3) Operations

The ultraviolet lamp of biological safety cabinet was turned on 30 minutes in advance for irradiation, and then ventilation was conducted for 3 minutes. The growth medium, detection medium, D-PBS and trypsin were pre-heated in a 37° C. thermostat water bath, surface-disinfected with alcohol and placed same in the biological safety cabinet. The cells with a confluence of about 80% were selected, and placed in the biological safety cabinet; after the old medium was drawn off, the cells were rinsed with D-PBS, which was then aspirated; and the rinsed cells were digested with trypsin for 2 to 3 min, added with the growth medium for neutralization, and centrifuged at 1200 rpm for 3 min. The centrifugal supernatant was drawn off, and 4 mL of detection medium was used for homogeneously mixing. 100 ul was used for counting, wherein 50 ul of cell liquid was taken out, and 50 ul of Trypan Blue Stain was added for mixing homogeneously and then counting. According to the number previously determined, the cells are plated at a density of 80 ul/well in a 96 well plate, wherein only well E11, F11 and G11 were only added with 80 ul of detection medium, and marginal wells were filled with 150 ul of DPBS. The dilution of the antibody solution comprises: using a detection medium to prepare 300 ul of the test sample solution with an initial concentration of 5 uM in the first column of a 96 well plate (type V); adding 210 ul of the detection medium into the second column to the tenth column from behind; adding 30 ul of the homogeneously-mixed solution from the first column to the second column; mixing same homogeneously by pipetting up and down 10 times with a pipette; and discarding the pipetting head, and repeating the operation for the next 7 concentrations in sequence; after 24-h plating, adding diluted antibodies at 20 ul per well and setting controls by only adding 20 ul of the detection medium to column 11; repeating each concentration in 2 wells; and after the addition, mixing same homogeneously using a cell vortex shaker at 550 rpm for 3 min.

4) Detection 4 days later, MTS reagent was taken out, thawed at room temperature away from light, and homogeneously mixed in a vortex mixer. In a biological safety cabinet, 20 μL of CellTiter 96@One Solution Reagen MTS reagent was added along the side wall of wells for each 100 μL of the cell culture volume. The MTS solution was homogeneously mixed by gently patting the panel surface, and placed in a cell incubator away from light for 2 h for standing incubation. After the completion of the reaction, the 96 well plate was taken out, and measured for the absorbance value at OD490 nm using a microplate reader; and data recording, sorting and storage were performed.

5) Results

| Number | SKBR3 IC50 (nM) | SKOV3 IC50 (nM) | NCI-N87 IC50 (nM) |
|---|---|---|---|
| Tras - 0303 | 0.37 | 1.43 | 7.92 |
| Trastuzumab | >1000 | >1000 | 200-1000 |

The invention claimed is:

1. A non-natural amatoxin-antibody conjugate, comprising a toxin moiety having a structural formula (I) or a pharmaceutically acceptable salt thereof, and a biomacromolecule moiety A having a binding affinity to a target, (I)

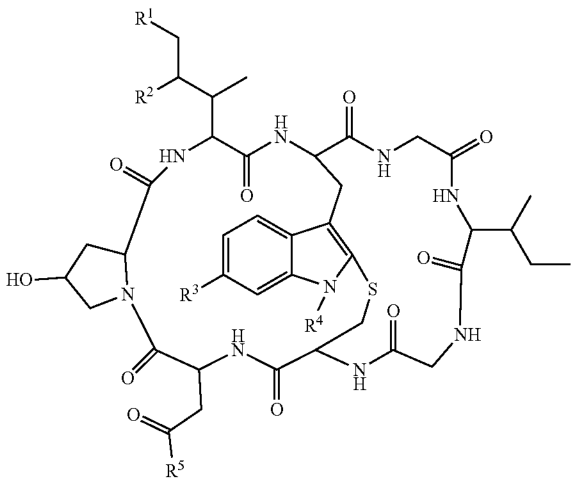

wherein:

$R^1$ is H, —OH or —O-L-A;

$R^2$ is H or —OH;

$R^3$ is $OC_{1-6}$ alkyl;

$R^4$ is H or -L-A-NH2 or —OH;

$R^5$ is —$NH_2$, —OH, —NH-L-A or —O-L-A;

wherein O is an oxygen atom, N is a nitrogen atom and H is a hydrogen atom, wherein A represents a biomacromolecule moiety, and wherein L is a linker, comprising the following structure:

$-L_1-[L_2]_m-[AA]_n-L_3-$, wherein: $L_1$ is a linker for connecting to A, and wherein $L_1$ is selected from:

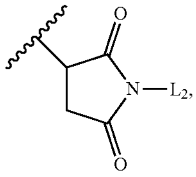

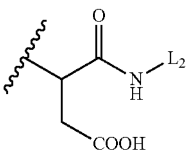,

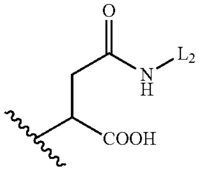,

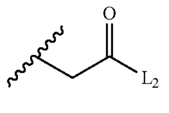 or 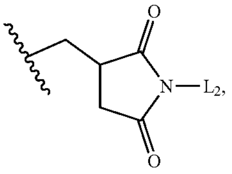

wherein a wavy line connects to A;

$L_2$ is a spacer connecting $L_1$ to AA; m is an integer selected from 1-6; $L_3$ is a structural fragment connecting to the toxin moiety; AA is a structural fragment consisting of 1 to 6 amino acids, and n is 0 or 1.

2. The non-natural amatoxin-antibody conjugate claim 1, wherein $R^1$ is —OH;

$R^2$ is —OH;

$R^3$ is $OCH_3$;

$R^4$ is H;

$R^5$ is —NH-L-A, and wherein L is

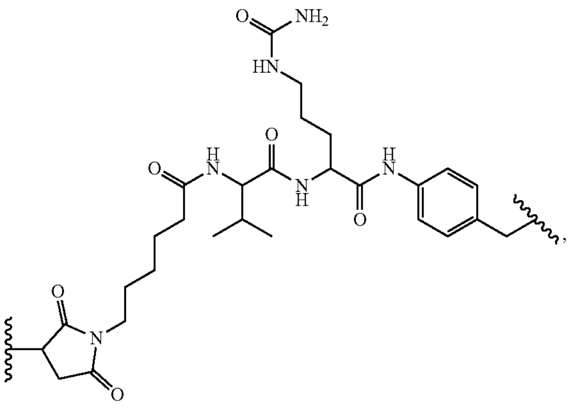 [SMILES: *Cc1ccc(NC(=O)C(CCCNC(N)=O)NC(=O)C(NC(=O)CCCCCN2C(=O)CC(*)C2=O)C(C)C)cc1]

and wherein the left-side wavy line connects to A, and the right-side wave line connects to NH in $R^5$.

3. The non-natural amatoxin-antibody conjugate of claim 1, wherein A comprises an antibody or its antigen-binding fragment thereof, or a nucleic acid aptamer.

4. The non-natural amatoxin-antibody conjugate of claim 3, wherein the antibody or its antigen-binding fragment thereof-comprises a chimeric antibody, a deimmunized antibody, a humanized antibody, a human antibody, a bispecific antibody, a tetra-specific antibody, a nanobody or their antigen-binding fragments thereof.

5. The non-natural amatoxin-antibody conjugate of claim 3, wherein the antigen-binding fragment is selected from the group consisting of Fab, F(ab'), Fd, Fv, a single-chain Fv or a disulfide-linked Fv(dsFv).

6. The non-natural amatoxin-antibody conjugate of claim 1, wherein only one of $R^1$, $R^4$ and $R^5$ comprises a -L-A structure.

7. The non-natural amatoxin-antibody conjugate of claim 1, wherein $R^1$ corresponds to —H or —OH;

$R^2$ corresponds to —H or —OH;

$R^3$ corresponds to —$OC_{1-6}$ alkyl;

$R^4$ corresponds to —$NH_2$ or —OH;

$R^5$ corresponds to —NH-L-A or —O-L-A.

8. The non-natural amatoxin-antibody conjugate of claim 1, wherein $L_2$ is a substituted or unsubstituted C1-C6 alkyl, a substituted or unsubstituted C3-C20 cycloalkyl, a substituted or unsubstituted C3-C20 heterocycloalkyl, a substituted or unsubstituted C5-C20 aryl, a substituted or unsubstituted C5-C20 heteroaryl, or —$(CH_2CH_2O)a$-, wherein a is an integer selected from 1 to 20.

9. The non-natural amatoxin-antibody conjugate of claim 8, wherein the $L_2$ substitution comprises a substitution with a hydroxyl group, a sulfydryl group, halogen, a carboxyl group, an amino group, a phosphate group, a nitro group, a cyano group, a sulfo group, or a substituted or unsubstituted C1-C6 alkyl.

10. The non-natural amatoxin-antibody of claim 9, wherein the further substituted comprises a substitution with a hydroxyl group, a sulfydryl group, halogen, a carboxyl group, an amino group, a phosphate group, a nitro group, a cyano group, or a sulfo group.

11. The non-natural amatoxin-antibody conjugate of claim 1, wherein the amino acids are L-amino acids selected from glycine, alanine, valine, leucine, isoleucine, phenylalanine, proline, tryptophan, serine, tyrosine, cysteine, methionine, asparagine, glutamine, threonine, aspartate, glutamate, lysine, arginine or histidine.

12. The non-natural amatoxin-antibody conjugate of claim 1, wherein the amino acids are selected from phenylalanine, citrulline, valine, lysine, serine, glutamate, aspartate or glycine.

13. The non-natural amatoxin-antibody conjugate of claim 1, wherein $L_3$ comprises

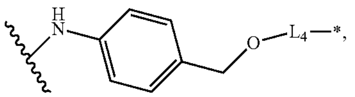

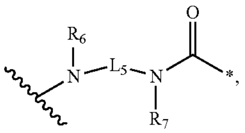

or

-continued

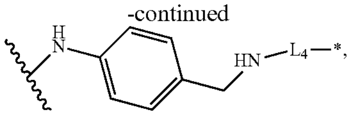

wherein a wavy line represents the connection to AA and an asterisk represents the connection to the toxin moiety, wherein n is 1, wherein L4 is a carbonyl group or a single bond, wherein L5 is C2-C12 alkyl, and wherein R6 and R7 are each independently selected from hydrogen or C1-C6 alkyl.

14. The non-natural amatoxin-antibody conjugate of claim 13, wherein L4 is a carbonyl group.

15. A pharmaceutical composition comprising the non-natural amatoxin-type antibody conjugate of claim 1 and a pharmaceutically acceptable carrier.

16. A method of making the pharmaceutical composition of claim 15, comprising combining the non-natural amatoxin-type antibody conjugate of claim 1 with the pharmaceutically acceptable carrier.

17. The pharmaceutical composition of claim 15, wherein the pharmaceutical composition is an anti-lung cancer drug, an anti-renal cancer drug, an anti-urethral cancer drug, an anti-colorectal cancer drug, an anti-prostate cancer drug, an anti-glioblastoma drug, an anti-ovarian cancer drug, an anti-pancreatic cancer drug, an anti-breast cancer drug, an anti-melanoma drug, an anti-liver cancer drug, an anti-bladder cancer drug, an anti-malignant lymphoma drug, an anti-leukemia drug, an anti-gastric cancer drugs or an anti-esophageal cancer drug.

* * * * *